United States Patent
Bavetsias et al.

(10) Patent No.: US 7,297,701 B2
(45) Date of Patent: Nov. 20, 2007

(54) ANTI-CANCER CYCLOPENTA [G]QUINAZOLINE COMPOUNDS

(75) Inventors: Vasilios Bavetsias, Sutton (GB); Ann L Jackman, Horsham (GB)

(73) Assignee: BTG International Limited, London (GB)

( * ) Notice: Subject to any disclaimer, the term of this patent is extended or adjusted under 35 U.S.C. 154(b) by 366 days.

(21) Appl. No.: 10/487,871

(22) PCT Filed: Aug. 30, 2002

(86) PCT No.: PCT/GB02/03979

§ 371 (c)(1),
(2), (4) Date: Jul. 16, 2004

(87) PCT Pub. No.: WO03/020748

PCT Pub. Date: Mar. 13, 2003

(65) Prior Publication Data
US 2004/0242606 A1 Dec. 2, 2004

(30) Foreign Application Priority Data

Aug. 31, 2001 (GB) .................. 0121151.5
Dec. 7, 2001 (GB) .................. 0129387.7

(51) Int. Cl.
*A01N 43/54* (2006.01)
*A61K 31/505* (2006.01)
*C07D 239/00* (2006.01)
*C07D 239/70* (2006.01)
*C07D 471/00* (2006.01)
*C07D 487/00* (2006.01)

(52) U.S. Cl. ..................... 514/267; 544/249
(58) Field of Classification Search ............ None
See application file for complete search history.

(56) References Cited

U.S. PATENT DOCUMENTS 5,747,499 A * 5/1998 Bavetsias et al. ........... 514/267

FOREIGN PATENT DOCUMENTS

WO    WO 94 11354 A1    5/1994
WO    WO 95 30673 A1    11/1995
WO    WO 00 50417 A1    8/2000

OTHER PUBLICATIONS

Bavetsias, V. et al; "Design and Synthesis of Cyclopenta'g!quinazoline-based antifolates as inhibitors of thymidylate synthase and potential antitumor agents"; *Journal of Medicinal Chemistry*, American Chemical Society, Wash., US, vol. 43, No. 10, 2000, pp. 1910-1926-26; XP002187697.

Melin, C. et al; "Novel cyclopenta'g!quinazoline dipeptide antifolates: Thymidylate synthase inhibitors with activity independent of the reduced folate carrier and folylpolyglutamate synthetase", *Chemistry and Biology of Peteridines and Folates*; 1997, Proceedings of the Int'l Symposium on Pteridines and Folates, 11th, Berchtesgaden, Germany; Eds. Pfleiderer, Wolfgang; Rokos, Hartmut; Publ.: Blackwell Wissenschafts-Verlag; Jun. 15-20, 1997, pp. 139-144, XP009000407.

Bavetsias, V., et al; "Synthetis and antitumour activity of cyclopenta'g!quinazoline-based antifolates, a novel class of thymidylate synthase (TS) inhibitors"; *Chemistry and Biology of Pteridines and Folates 1997*, Proceedings of the Int'l Symposium on Pteridines and Folates, 11th, Berchtesgaden, Germany, Eds.: Pfleiderer, Wolfgang, Rokos, Hartmut; Publ.: Blackwell Wissenschafts-Verlag, Jun. 15-20, 1997, pp. 205-208, XP009000408.

Roth, K.D., et al; "Nicholas Reactions of Amines"; *Tetrahedron Letters* (1993) vol. 34, No. 18, pp. 2919-2911.

Theti et al; *Clinical Cancer Research*, vol. 5, Nov. 1999 (Supplemental) at #566.

Jackman et al; *Proceedings of the American Association for Cancer Research*41, Mar. 2000 at #33.

* cited by examiner

*Primary Examiner*—James O. Wilson
*Assistant Examiner*—Erich Leeser
(74) *Attorney, Agent, or Firm*—Nixon & Vanderhye

(57) ABSTRACT

Cyclopenta[g]quinazolines of the formula (I):—wherein: A is a group OR or $NR^0R^1$ wherein $R^0$ and $R^1$ are each independently hydrogen $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^0$ and $R^1$ together with the intermediate N form a five- or six-membered heterocyclic ring, p is an integer in the range 1 to 4, $R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl; $Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy, and $R^3$ is a group of one of the following formulae: $-A^1-Ar^2-A^2-Y^1-A^5-CON(R)CH(Y^4)Y^5-A^8-X-Ar^4$ and pharmaceutically acceptable salts or esters thereof are of therapeutic value particularly in the treatment of cancer (I)

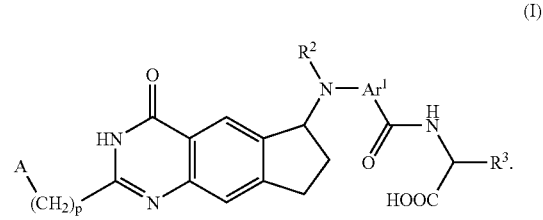

2 Claims, No Drawings

ANTI-CANCER CYCLOPENTA [G]QUINAZOLINE COMPOUNDS

This application is the U.S. National Phase of International Application PCT/GB02/03979, filed 30 Aug. 2002, which designated the U.S.

This invention relates to novel anti-cancer agents and more particularly it relates to cyclopenta[g]quinazoline derivatives which possess antiproliferative activity.

One group of anti-cancer agents comprises antimetabolites having antifolate activity, such as the dihydrofolate reductase inhibitor, methotrexate and the thymidylate synthase (TS) inhibitors CB3717, raltitrexed and ZD9331. CB3717 is described and claimed in EP-B-0031237, raltitrexed in EP-B-0239362 and ZD9331 in EP-B-0562734. All of these TS inhibitors have demonstrable clinical activity in a range of solid tumours (see *Cancer Treatment Reports*, 1986, 70, 1335 and Beale et al., "Tomudex: Clinical Development" in *Antifolate Drugs in Cancer Therapy* (ed. Jackman), Humana Press, Totowa, N.J., USA, pp. 177-181, 1999). Side-effects of raltitrexed and ZD9331 are predominantly related to inhibition of TS in gut and bone-marrow.

TS catalyses the methylation of deoxyuridine monophosphate to produce thymidine monophosphate which is required for DNA synthesis. The anticancer activity of these agents may be assessed in vitro by determining their inhibitory effect on that enzyme, and in cell cultures by their inhibitory effect on a range of mouse and human cancer cell lines (see Boyle et al., "ZD9331: Preclinical and clinical studies" in *Antifolate Drugs in Cancer Therapy* (ed. Jackman), Humana Press, Totowa, N.J., USA, pp. 243-260, 1999 and Hughes et al., "Raltitrexed (Tomudex), a highly polyglutamatable antifolate thymidylate synthase inhibitor: design and preclinical activity" in *Antifolate Drugs in Cancer Therapy* (ed. Jackman), Humana Press, Totowa, N.J., USA, pp. 147-165, 1999).

More recently, cyclopenta[g]quinazoline derivatives showing a good level of activity both as regards their ability to inhibit TS and also as regards their anticancer activity against various cell lines have been developed.

WO-A-94/11354 (British Technology Group Limited) discloses tricyclic compound of formula:

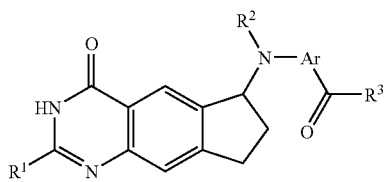

wherein $R^1$ is hydrogen, amino, $C_{1-4}$ alkyl, $C_{1-4}$ alkoxy, $C_{1-4}$ hydroxyalkyl or $C_{1-4}$ fluoroalkyl;

$R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

Ar is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group of one of the following formulae:

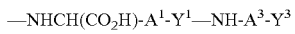
—NHCH(CO$_2$H)-A$^1$-Y$^1$—NH-A$^3$-Y$^3$ or $R^3$ is a N-linked naturally-occurring amino acid selected from the group consisting of L-alanine, L-leucine, L-isoleucine, L-valine and L-phenylalanine. Among the compounds disclosed is the L-Glu-γ-D-Glu compound CB300638, also mentioned in *Clinical Cancer Research*, 5, November 1999 (Supplement) at #566 (Theti et al.) and *Proceedings of the American Association for Cancer Research*, 41, March 2000 at #33 (Jackman et al.), as well as in *J. Med. Chem.*, 2000, 43, 1910-1926, where it is disclosed on page 1923 as compound 7b.

WO-A-95/30673 (British Technology Group Limited) discloses cyclopenta[g]quinazolines of formula:

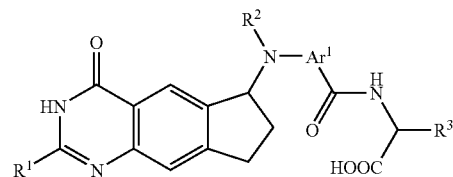

wherein $R^1$ is hydrogen, amino, $C_{1-4}$ alkyl, $C_{1-4}$ alkoxy, $C_{1-4}$ hydroxyalkyl or $C_{1-4}$ fluoroalkyl;

$R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

$Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group of one of the following formulae:

-A$^1$-Ar$^2$-A$^2$-Y$^1$-A$^5$-CON(R)CH(Y$^4$)Y$^5$-A$^8$-X—Ar$^4$

The α-isoform of the folate receptor (α-FR; membrane-associated folate-binding protein) is a glycosylphosphatidylinositol anchored cell membrane protein that has very high affinity for folic acid and the more biologically relevant reduced-folates (Kd ~0.1 nM). The mechanism of folate internalisation is receptor-mediated endocytosis. The α-FR is overexpressed in many carcinomas, particularly those of ovarian origin where it is overexpressed highly and homogeneously in 90% of cases; see *Cancer Res.* 51, 5329-5338, 1991 (Campbell et al., 1991). Furthermore, high α-FR expression has been linked to aggressive, platinum resistant disease and poor prognosis—see *Int. J. Cancer* 74, 193-198, 1997 and *Int. J. Cancer* 79, 121-126, 1998 (both Toffoli et al.). The β-isoform is widely expressed in tumours of epithelial and non-epithelial origin with expression levels being generally low/moderate and high, respectively, reviewed in *Critical Rev. Therap. in Drug Carrier Systems* 15, 587-627, 1998 (Reddy and Low).

Folate receptors (α and β) are expressed in some adult normal tissues (low to moderate expression). Significant expression of the α-FR is largely restricted to kidney proximal tubules and choroid plexus although it is suggested that it is localised to the apical membrane surface in these organs and therefore may not play a significant role in folate uptake from blood (Reddy and Low, ibid.). There may be a specialised function of the α-FR in the proximal tubules of the kidney to salvage folates that escape in the filtrate.

The α-FR is hypothesised to be involved in cell signalling pathways. For example, in IGROV-1 ovarian carcinoma cells, immunoprecipitation experiments have shown that the α-FR is associated in membranes with the G protein $G_{\alpha 1-3}$, and the non-receptor kinase lyn.

High FR expression in some tumours relative to normal tissues is being exploited in several areas of cancer medicine, including the selective tumour delivery of conjugates of folic acid and toxins, liposomes, imaging or cytotoxic agents (Reddy and Low, ibid). For example, folic acid-deferroxamine. [111]In conjugates are detected only in FR-expressing turnouts and not normal tissues of mice, with the exception of kidney epithelial cells. The high selectivity of this approach resides in the very low and high affinities of folic acid (not a major component of plasma) for the RFC (reduced-folate carrier) and FR respectively. Thus antifolate drugs with similarly low and high affinity for the RFC and α-FR respectively could be highly selective for α-FR over-expressing tumours relative to normal tissues. In contrast with the folic acid conjugates they would not require intracellular cleavage to be active.

We have now discovered that certain compounds within the general class of cyclopenta[g]quinazolines have an unexpectedly high level of selectivity for α-folate receptor expressing human tumour cell lines. Accordingly the present invention comprises a cyclopenta[g]quinazoline of formula (I):

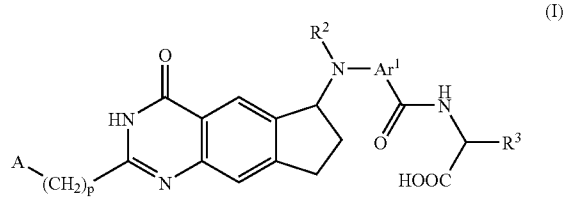

wherein:

A is a group OR or $NR^0R^1$ wherein $R^0$ and $R^1$ are each independently hydrogen $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^0$ and $R^1$ together with the intermediate N form a five- or six-membered heterocyclic ring;

p is an integer in the range 1 to 4;

$R^2$ is hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl;

$Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy; and $R^3$ is a group of the formulae:

-$A^1$-$Ar^2$-$A^2$-$Y^1$ in which $A^1$ is a bond between the α-carbon atom of the group —CO—NH—CH(CO$_2$H)— and $Ar^2$ or is a $C_{1-2}$ alkylene group;

$Ar^2$ is phenylene, tetrazolediyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^2$ is a $C_{1-3}$ alkylene or $C_{2-3}$ alkenylene group; and $Y^1$ is carboxyl, tetrazol-5-yl, N-($C_{1-4}$ alkylsulfonyl)carbamoyl, N-(phenylsulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; or $Y^1$ is a group of the formula:

—CON(R)CH($Y^2$)$Y^3$ in which R is hydrogen, $C_{1-4}$ alkyl, $C_{3-4}$ alkenyl or $C_{3-4}$ alkynyl;

$Y^2$ is carboxy, tetrazol-5-yl, N-($C_{1-4}$ alkylsulfonyl)carbamoyl, N-(phenylsulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; and $Y^3$ is the residue of a naturally occurring amino acid NH$_2$CH(CO$_2$H)$Y^3$; or $Y^3$ is a group of the formula:

-$A^4$-CO$_2$H in which $A^4$ is a $C_{2-6}$ alkylene group;

$R^3$ is a group of the formula:

-$A^5$-CON(R)CH($Y^4$)$Y^5$ in which $A^5$ is a $C_{1-6}$ alkylene group and R is as defined above;

$Y^4$ is carboxy, tetrazol-5-yl, N-($C_{1-4}$ alkylsulfonyl)carbamoyl, N-(phenylsulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; and $Y^5$ is the residue of a naturally occurring amino acid NH$_2$CH(CO$_2$H)$Y^5$; or $Y^5$ is a group of the formula:

-$A^4$-CO$_2$H in which $A^4$ is as defined above; or $Y^5$ is a group of the formula:

-$A^6$-$Ar^3$-$A^7$-$Y^6$ in which $A^6$ is a bond between the α-carbon atom of the group -$A^5$-CON(R)CH($Y^4$)— and $Ar^3$ or is a $C_{1-2}$ alkylene group;

$Ar^3$ is phenylene, tetrazolediyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^7$ is a $C_{1-3}$ alkylene or $C_{2-3}$ alkenylene group; and $Y^6$ is carboxy, tetrazol-5-yl, N-($C_{1-4}$ alkylsulfonyl)carbamoyl, N-(phenylsulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; or $R^3$ is a group of the formula:

-$A^8$-X—$Ar^4$ in which $A^8$ is a $C_{1-4}$ alkylene group;

X is sulfinyl, sulfonyl or methylene; and $Ar^4$ is 1,2,3-triazol-4-yl, 1,2,4-triazol-3-yl or, except when X is methylene, tetrazol-5-yl;

the compound (I) optionally being in the form of a pharmaceutically acceptable salt or ester.

In this specification the terms alkyl, alkenyl, alkynyl and alkylene include both straight and branched chain groups but references to individual alkyl or alkylene groups, such as "propyl", are specific for the straight chain group only. An analogous convention applies to other generic terms. Moreover, the numbering system used for the cyclopenta[g]quinazoline nucleus is the conventional one as shown below:

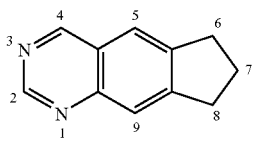

Amino-acid residues are designated herein in the standard manner (*Pure and Applied Chemistry*, 1974, 40, 317 and *European Journal of Biochemistry*, 1984, 138, 9). Thus, for example, 7-glutamyl denotes the radical $H_2NCH(CO_2H)CH_2CH_2CO—$ or $—NHCH(CO_2H)CH_2CH_2CO—$ according to the context, the carbon atoms in these radicals being numbered from the carbon atom of the α-carboxy group as position 1.

It will be observed that a cyclopenta[g]quinazoline of the invention contains at least two asymmetric carbon atoms [present at the point of attachment of the group $—N(R^2)—$ to the tricyclic ring system and at the α-carbon atom of the group $—CONHCH(CO_2H)—$] and can therefore exist in racemic and optically active forms. It is to be understood that this invention encompasses both racemic and optically active forms of the physiologically active cyclopenta[g]quinazolines, it being a matter of common general knowledge how such optically active forms may be obtained by stereospecific synthesis or by separation of a mixture of isomeric compounds. It will be appreciated that one isomer may be of more interest than another due to the nature of the activity which it exhibits or due to superior physical properties, for example aqueous solubility.

It is also to be understood that a cyclopenta[g]quinazoline of the formula (I) may exhibit the phenomenon of tautomerism and that the formulae shown in this specification represent only one of the possible tautomeric forms. Moreover, it will be appreciated that when, for example, $Y^1$, $Y^2$, $Y^4$ or $Y^6$ is a tetrazol-5-yl group, that group may be in the form of a 1H-tetrazol-5-yl group or a 2H-tetrazol-5-yl group. It is to be understood therefore that the invention is not limited merely to any one tautomeric form which is illustrated.

It is also to be understood that certain cyclopenta[g]quinazolines of the formula (I) can exist in solvated as well as unsolvated forms such as, for example, hydrated forms.

A suitable value for $R^0$, $R^1$ or $R^2$ when it is $C_{1-4}$ alkyl, or for a $C_{1-4}$ alkyl substituent which may be present on $Ar^1$, $Ar^2$ or $Ar^3$ or on a phenyl group-containing group $Y^1$, $Y^2$, $Y^4$ or $Y^6$ present in $R^3$, or for a group R present in $R^3$ when it is $C_{1-4}$ alkyl, is, for example, methyl, ethyl, propyl or isopropyl.

A suitable value for a $C_{1-4}$ alkoxy substituent which may be present on $Ar^1$, $Ar^2$ or $Ar^3$ or on a phenyl-containing group $Y^1$, $Y^2$, $Y^4$ or $Y^6$ is, for example, methoxy, ethoxy, propoxy, isopropoxy or butoxy.

A suitable value for a halogeno substituent which may be present on $Ar^1$, $Ar^2$ or $Ar^3$ or on a phenyl-containing group $Y^1$, $Y^2$, $Y^4$ or $Y^6$ is, for example, fluoro, chloro or bromo.

A suitable value for $R^0$, $R^1$ and $R^2$ when it is $C_{3-4}$ alkenyl or for a group R present in $R^3$ when it is alkenyl, is, for example, prop-2-enyl, but-2-enyl, but-3-enyl or 2-methylprop-2-enyl; and when it is $C_{3-4}$ alkynyl is, for example, prop-2-ynyl or but-3-ynyl.

A suitable value for $R^0$, $R^1$ and $R^2$ when it is $C_{2-4}$ hydroxyalkyl is, for example, 2-hydroxyethyl or 3-hydroxypropyl; when it is $C_{2-4}$ halogenoalkyl is, for example, 2-fluoroethyl, 2-chloroethyl, 2-bromoethyl, 3-fluoropropyl, 3-chloropropyl or 3-bromopropyl; and when it is $C_{1-4}$ cyanoalkyl is, for example, cyanomethyl, 2-cyanoethyl or 3-cyanopropyl.

When $R^0$ and $R^1$ together with the intermediate N form a five- or six-membered heterocyclic ring, this may bear substituents, but the ring is preferably an unsubstituted saturated ring such as pyrrolidine or piperidine.

A suitable value for $Ar^1$, $A^2$ or $Ar^3$ when it is phenylene is, for example, 1,3- or 1,4-phenylene, especially 1,4-phenylene.

A suitable value for $Ar^1$, $Ar^2$ or $Ar^3$ when it is thiophenediyl is, for example, thiophene-2,4-diyl or thiophene-2,5-diyl; when it is thiazolediyl is, for example thiazole-2,4-diyl or thiazole-2,5-diyl; when it is pyridinediyl is, for example, pyridine-2,4-diyl, pyridine-2,5-diyl, pyridine-2,6-diyl or pyridine-3,5-diyl; and when it is pyrimidinediyl is, for example, pyrimidine-2,4-diyl, pyrimidine-2,5-diyl or pyrimidine-4,6-diyl.

As indicated, $Ar^1$ and a phenylene group $Ar^2$ or $Ar^3$ or a phenyl group in $Y^1$ may carry one or two substituents. A preferred level of substitution in $Ar^1$, where substitution is present, is either two substituents or especially one substituent; and the one or two substituents may conveniently be at positions adjacent to the atom bonded to the group $—CONHCH(CO_2H)—R^3$, halogeno substituents such as fluoro being preferred. A preferred level of substitution on a phenylene group $Ar^2$ or $Ar^3$ or on a phenyl group in $Y^1$, where substitution is present, is one substituent.

When $R^3$ is a group of the formula:

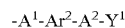

$-A^1-Ar^2-A^2-Y^1$ a suitable value for $A^1$ when it is a $C_{1-2}$ alkylene group is, for example methylene or ethylene and for $A^2$ when it is a $C_{1-3}$ alkylene group is, for example, methylene, ethylene or trimethylene. A suitable value for $A^2$ when it is a $C_{2-3}$ alkenylene group is, for example, vinylene or especially propenylene ($—CH_2CH=CH—$ or $—CH=CH(CH_2—)$). A preferred value for both $A^1$, when it is not a bond, and for $A^2$ is methylene or ethylene. Suitable values for $Ar^2$ include those which have been discussed hereinbefore, such as thiophenediyl or most especially phenylene, or additionally tetrazole-1,5-diyl or tetrazole-2,5-diyl. A suitable value for $Y^1$ or for $Y^2$ in a group $Y^1$ of formula $—CON(R)CH(Y^2)Y^3$ when it is N-($C_{1-4}$ alkylsulfonyl)carbamoyl is, for example, N-methylsulfonylcarbamoyl, N-ethylsulfonylcarbamoyl or N-propylsulfonylcarbamoyl.

In a group $Y^1$ of formula $—CON(R)CH(Y^2)Y^3$ suitable values for $C_{1-4}$ alkyl, $C_{3-4}$ alkenyl and $C_{3-4}$ alkynyl groups R have been discussed hereinbefore but R is preferably either methyl or especially hydrogen; a suitable value for $Y^3$ when it is the residue of a naturally occurring amino acid is the residue of alanine ($Y^3=CH_3$), arginine ($Y^3=(CH_2)_3NHC(H_2)=NH$), aspartic acid ($Y^3=CH_2CO_2H$), cysteine ($Y^3=CH_2SH$), isoleucine ($Y^3=CH(CH_3)CH_2CH_3$), leucine ($Y^3=CH_2CH(CH_3)CH_3$), ornthine ($Y^3=(CH_2)_3NH_2$), phenylalanine ($Y^3=CH_2C_6H_5$), serine ($Y^3=CH_2OH$) and valine ($Y^3=CH(CH_3)_2$) and especially glutamic acid ($Y^3=CH_2CH_2CO_2H$). A suitable value for $A^4$ when $Y^3$ is a group of the formula $-A^4-CO_2H$ is trimethylene, pentamethylene or hexamethylene, $A^4$ preferably being a $C_{3-6}$ alkylene group with especially suitable values for $Y^3$ being $—(CH_2)_nCO_2H$ where n is 3, 4 or 5.

A preferred value for $Y^1$ or for $Y^2$, $Y^4$ and $Y^6$, is tetrazol-5-yl or especially carboxy.

When $R^3$ is a group of the formula:

-$A^5$-CON(R)CH($Y^4$)$Y^5$ a suitable value for $A^5$ is, for example, methylene, ethylene, trimethylene, tetramethylene, pentamethylene or hexamethylene and a suitable value for R is as described hereinbefore. A suitable value for $Y^4$ when it is N-($C_{1-4}$ alkylsulfonyl)-carbamoyl is, for example, N-methylsulfonylcarbamoyl, N-ethylsulfonylcarbamoyl or N-propylsulfonylcarbamoyl.

A suitable value for $Y^5$ when it is the residue of a naturally occurring amino acid is alanine ($Y^5$=$CH_3$), arginine ($Y^5$=$(CH_2)_3$NHC($NH_2$)=NH), aspartic acid ($Y^5$=$CH_2CO_2H$), cysteine ($Y^5$=$CH_2SH$), isoleucine ($Y^5$=CH($CH_3$)$CH_2CH_3$), leucine ($Y^5$=$CH_2$CH($CH_3$)$CH_3$), ornithine ($Y^5$=$(CH_2)_3$$NH_2$), phenylalanine ($Y^5$=$CH_2C_6H_5$), serine ($Y^5$=$CH_2$OH), valine ($Y^5$=CH($CH_3$)$_2$), and especially glutamic acid ($Y^5$=$CH_2CH_2CO_2H$). When $Y^5$ is a group of the formula -$A^4$-$CO_2H$, suitable values for $A^4$ and $Y^5$ are as described hereinbefore in relation to a group $Y^3$ of the formula -$A^6$-$CO_2H$.

A suitable value for $A^6$ in a group $Y^5$ of the formula -$A^6$-$Ar^3$-$A^7$-$Y^6$ is as described hereinbefore for $A^1$ and for $A^7$ is as described for $A^2$. A suitable value for $Ar^3$ is as described hereinbefore for $Ar^2$. A suitable value for $Y^6$ in such a group $Y^5$ when it is N-($C_{1-4}$ alkylsulfonyl)carbamoyl is, for example, N-methylsulfonylcarbamoyl, N-ethylsulfonylcarbamoyl or N-propylsulfonylcarbamoyl.

When $R^3$ is a group of the formula:

-$A^8$-X—$Ar^4$ a suitable value for $A^8$ is, for example, methylene, ethylene, trimethylene or tetramethylene.

Groups $R^3$ of particular value have the formula -$A^1$-$Ar^2$-$A^2$-$Y^1$, especially when $Y^1$ is a group not of the formula —CON(R)CH($Y^2$)$Y^3$, such as carboxy or tetrazol-5-yl.

Specific examples of such groups $R^3$ are groups -$A^1$-$Ar^2$-$A^2$-$Y^1$ in which $A^1$ is a bond or methylene or ethylene, $Ar^2$ is phenylene, thiophenediyl or tetrazolediyl, $A^2$ is methylene, ethylene or trimethylene and $Y^1$ is carboxy or tetrazol-5-yl.

Other groups $R^3$ of particular value have the formula -$A^5$-CON(R)CH($Y^4$)$Y^5$, especially when $Y^5$ is a group of the formula -$A^6$-$Ar^3$-$A^7$-$Y^6$ in which $Ar^3$ is phenylene, thiophenediyl or tetrazolediyl.

Specific examples of such groups $R^3$ are groups -$A^5$-CON(R)CH($Y^4$)-$A^6$-$Ar^3$-$A^7$-$Y^6$ in which $A^5$ is methylene or ethylene, R is hydrogen or methyl, $Y^4$ is carboxy or tetrazol-5-yl, $A^6$ is a bond or is methylene or ethylene, $Ar^3$ is phenylene, thiophenediyl or tetrazolediyl, $A^7$ is methylene, ethylene or trimethylene and $Y^6$ is carboxy or tetrazol-5-yl.

A suitable pharmaceutically-acceptable salt form of a cyclopenta[g]quinazoline of the invention is, for example, an acid addition salt with an inorganic or organic acid, for example hydrochloric, hydrobromic, trifluoroacetic or maleic acid; or an alkali metal, for example sodium, an alkaline earth metal, for example calcium, or ammonium, for example tetra(2-hydroxyethyl)ammonium, salt.

A suitable pharmaceutically-acceptable ester form of a cyclopenta[g]quinazoline of the invention is, for example, an ester with an aliphatic alcohol of up to 6 carbon atoms, for example a methyl, ethyl or tert-butyl ester.

It is to be understood that $R^3$ may contain several carboxy groups in addition to the carboxy group in the grouping —CONHCH($CO_2H$)—. When, for example, two carboxy groups are present in the cyclopenta[g]quinazoline, a salt or ester may be mono-acid-mono-salt or -ester, -di-salt or di-ester and when, for example, three carboxy groups are present a salt or ester may be mono-acid-di-salt or -ester, di-acid-mono-salt or -ester or even tri-salt or -ester.

Particularly preferred values for the various symbols $R^0$, $R^1$, $R^2$ and $Ar^1$ individually are as expressed for the preferred cyclopenta[g]quinazolines described hereinafter.

A preferred cyclopenta[g]quinazoline of the invention has the formula (I) wherein $R^0$ and $R^1$ are each independently hydrogen or $C_{1-4}$ alkyl, especially methyl;

wherein $R^2$ is ethyl, propyl, prop-2-enyl, prop-2-ynyl, 2-hydroxyethyl, 2-fluoroethyl, 2-bromoethyl or 2-cyanoethyl;

wherein $Ar^1$ is 1,4-phenylene which may optionally bear one or two substituents selected from the group consisting of chloro and especially fluoro, thiophene-2,5-diyl, thiazole-2,5-diyl or pyridine-2,5-diyl;

wherein $R^3$ is a group of the formula -$A^1$-$Ar^2$-$A^2$-$Y^1$ in which $A^1$ is a bond or is methylene or ethylene, $Ar^2$ is phenylene, $A^2$ is methylene, ethylene or trimethylene and $Y^1$ is a group of the formula:

—CON(R)CH($Y^2$)$Y^3$ in which R is hydrogen, $C_{1-4}$ alkyl, $C_{3-4}$ alkenyl or $C_{3-4}$ alkynyl;

$Y^2$ is carboxy, tetrazol-5-yl, N-($C_{1-4}$ alkylsulfonyl)carbamoyl, N-(phenylsulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; and $Y^3$ is the residue of a naturally occurring amino acid $NH_2$CH($CO_2H$)$Y^3$. Alternatively, a preferred cyclopenta[g]quinazoline of the invention has the formula (I) wherein:

$R^0$ and $R^1$ are each independently hydrogen or $C_{1-4}$ alkyl;

$R^2$ is ethyl, propyl, prop-2-enyl, prop-2-ynyl, 2-hydroxyethyl, 2-fluoroethyl, 2-bromoethyl or 2-cyanoethyl;

$Ar^1$ is 1,4-phenylene which may optionally bear one or two substituents selected from the group consisting of chloro, fluoro, thiophene-2,5-diyl, thiazole-2,5-diyl or pyridine-2,5-diyl;

$R^3$ is a group of the formula:

-$A^5$-CON(R)CH($Y^4$)$Y^5$ in which $A^5$ is a $C_{1-6}$ alkylene group and R is as defined above;

$Y^4$ is carboxy, tetrazol-5-yl, N-($C_{1-4}$ alkylsulfonyl)carbamoyl, N-(phenylsulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; and $Y^5$ is the residue of a naturally occurring amino acid $NH_2$CH($CO_2H$)$Y^5$.

A preferred value for p is 1.

A further preferred cyclopenta[g]quinazoline of the invention has the formula (I) wherein A is a group $OR^0$ in which $R^0$ is hydrogen or methyl;

wherein $R^2$ is ethyl or prop-2-ynyl; and wherein $Ar^1$ is 1,4-phenylene or 1,4-phenylene having a 2-fluoro substituent as in 2,6-difluoro-1,4-phenylene or especially 2-fluoro-1,4-phenylene or is pyridine 2,5-diyl; and $R^3$ is as just described above.

An especially preferred cyclopenta[g]quinazoline of the invention has the formula (I) wherein A is a group $OR^0$ in which $R^0$ is hydrogen or methyl;

wherein $R^2$ is ethyl or preferably prop-2-ynyl;
wherein $Ar^1$ is 1,4-phenylene or 2-fluoro-1,4-phenylene; and
wherein $R^3$ is the residue of an acid $NH_2.CH(COOH)R^3$ which comprises L-Glu-γ-D-Glu, i.e. N-L-γ-glutamyl-D-glutamic acid.

Other quinazolines of the invention of particular interest have the values of $R^0$, $R^1$, $R^2$, and $Ar^1$ and Ar in combination as indicated above but with $R^3$ having any value as indicated hereinbefore. However, specific particularly preferred cyclopenta[g]quinazolines of the invention are:

N-{N-{4-[N-((6RS)-2-methoxymethyl-4-oxo-3,4,7,8-tetrahydro-6H-cyclopenta[g]quinazolin-6-yl)-N-(prop-2-ynyl) amino]benzoyl}-L-γ-glutamyl}-D-glutamic acid;

N-{N-{4-[N-((6RS)-2-hydroxymethyl-4-oxo-3,4,7,8-tetrahydro-6H-cyclopenta[g]quinazolin-6-yl)-N-(prop-2-ynyl) amino]benzoyl}-L-γ-glutamyl}-D-glutamic acid; and N-{N-{4-[N-((6RS)-2-hydroxymethyl-4-oxo-3,4,7,8-tetrahydro-6H-cyclopenta[g]quinazolin-6-yl)-N-(prop-2-ynyl) amino]benzoyl}-L-γ-glutamyl}-N-methyl-L-glutamic acid;

or a pharmaceutically acceptable salt or ester thereof.

Although the compounds of the present invention can exist as a mixture of stereoisomers it is preferred that they are resolved into one optically active isomeric form. Such a requirement complicates the synthesis of the compounds and it is preferred therefore that they contain as few asymmetric carbon atoms as possible consistent with achieving the desired activity.

As indicated previously, however, the cyclopenta[g]quinazolines of the present invention contain at least two asymmetric carbon atoms. Of these, that at the 6 position of the ring system preferably has the 6S orientation rather than the 6R orientation, whilst the alpha carbon atom of the group —CONHCH($CO_2H$)— preferably has the L rather than the D configuration. The preferred compounds (I) described hereinbefore thus preferably have such a configuration at these two asymmetric carbon atoms or less preferably are a racemic mixture in which one or both of these asymmetric carbon atoms is unresolved.

The asymmetric carbon atom of a residue $R^3$ of the form $-A^1-Ar^2-A^2-CON(R)CH(Y^2)Y^3$ or $-A^5-CON(R)CH(Y^4)Y^5$ may be of the L- or D-configuration but the amide bond will be stabilised in vivo when it is of the D-configuration as it will also be when R is other than hydrogen. When $Y^3$ or $Y^5$ is the residue of a naturally occurring amino acid, however, the amino acid intermediate for the synthesis of the cyclopenta[g]quinazoline will of course be more readily available when this asymmetric carbon atom is of the L-configuration.

A cyclopenta[g]quinazoline of the invention may be prepared by any process known to be applicable to the preparation of chemically-related compounds.

As stated above, cyclopenta[g]quinazolines of the present invention are believed to function as anti-cancer agents at least in part due to their ability to inhibit the enzyme thymidylate synthase. This anti-cancer activity may be assessed, for example, using one or more of the procedures set out below:

(a) An in vitro assay which determines the ability of a test compound to inhibit the enzyme thymidylate synthase. Thymidylate synthase may be obtained in partially purified form from L1210 mouse leukemia cells and utilised in the assay using the procedures described by Jackman et al. (*Cancer Res.*, 1986, 46, 2810) and Sikora et al. (*Biochem. Pharmacol.*, 1988, 37, 4047);

(b) An assay which determines the ability of a test compound to bind to the α-FR relative to that of folic acid, using mouse L1210-FBP cells (α-FR expression) in the procedure described by Westerhof et al. (*Cancer Res.*, 1991, 51, 5507-5513);

(c) An assay which determines the ability of a test compound to inhibit the growth of human tumour cell lines expressing the α-FR (A431-FBP vulvular carcinoma transfected with the α-FR; KB nasopharengeal carcinoma);

(d) An assay which determines the ability of a test compound to inhibit the growth of human tumour cell lines not expressing the α-FR (A431 neo-transfected);

(e) An assay confirming or demonstrating that compound-induced growth inhibition is largely attributable to α-FR mediated uptake into KB or A431-FBP cells. This involves the co-addition of an excess of folic acid (1 μM) to compete with the compounds for FR but not RFC binding.

Although the pharmacological properties of the cyclopenta[g]quinazolines of the invention depend on their detailed structure, in general the cyclopenta[g]quinazolines of the invention possess activity in one or more of the above tests (a) to (d) as indicated below:

| | |
|---|---|
| Test (a) | $IC_{50}$ in the range, for example, 0.0001-1 μM; |
| Test (b) | Inverse relative affinity in the range, for example, 0.05-5 (values geater than 1 implies binding is greater than that of folic acid and values less that 1 implies binding weaker than that of folic acid); |
| Test (c) | $IC_{50}$ in the range, for example, 0.001-10 μM; |
| Test (d) | $IC_{50}$ in the range, for example, 0.01-100 μM; |
| Test (e) | $IC_{50}$ at least 10-fold higher than that seen in test (b) for the same cell line. |

A cyclopenta[g]quinazoline of the present invention may itself be active or it may be a pro-drug which is converted in vivo to an active compound. A cyclopenta[g]quinazoline of the invention may be administered to a warm-blooded animal, including a human, in the form of a pharmaceutical composition which comprises the cyclopenta[g]quinazoline in association with a pharmaceutically-acceptable diluent or carrier.

The composition may be in a form suitable for oral use, for example a tablet, capsule, aqueous or oily solution, suspension or emulsion; a form suitable for topical use, for example a cream, ointment, gel or aqueous or oily solution or suspension; a form suitable for nasal use, for example a snuff, nasal spray or nasal drops; a form suitable for vaginal or rectal use, for example a suppository; a form suitable for administration by inhalation, for example as a finely divided powder such as a dry powder, a microcrystalline form or a liquid aerosol; a form suitable for sub-lingual or buccal use, for example a tablet or capsule; or a form suitable for parenteral use (including intravenous, subcutaneous, intramuscular, intravascular or infusion use), for example a sterile aqueous or oily solution, emulsion or suspension. In general the above compositions may be prepared in a conventional manner using conventional excipients.

The composition may contain, in addition to the cyclopenta[g]quinazoline of the invention, one or more other anti-cancer substances selected from, for example, other antimetabolites, DNA interacting agents, signal transduction inhibitors or other inhibitors of deregulated pathways in tumours.

The cyclopenta[g]quinazoline will normally be administered to a warm-blooded animal at a dose within a range of 50-25000, particularly 50-5000, mg per square metre body area of the animal, i.e. approximately 1500, particularly 1-100, mg/kg. Where desired, however, dosages outside this range may be employed and, in particular, where the preferred mode of administration involving subcutaneous infusion is used then the does range may be increased to 1-1000 mg/kg. Preferably a daily dose in the range 10-250 mg/kg is employed, particularly 30-150 mg/kg. However, the daily dose will necessarily be varied depending upon the host treated, the particular route of administration and the severity of the illness being treated. Accordingly, the optimum dosage may be determined by the practitioner who is treating any particular patient.

Accordingly the present invention also includes a method for aiding regression and palliation of cancer in a patient, particularly a warm-blooded animal such as a human, in need of such treatment, which comprises administering to said patient an effective amount of a cyclopenta[g]quinazoline as defined hereinbefore. The invention also provides the use of such a cyclopenta[g]quinazoline in the manufacture of a novel medicament for use in the treatment of cancer.

Cyclopenta[g]quinazolines of the present invention are of interest for a wide range of anti-tumour activities particularly the treatment of ovarian cancer.

In view of the activity shown by antimetabolites such as aminopterin and methotrexate, which is discussed hereinbefore, the cyclopenta[g]quinazolines of the present invention are also of interest for use in the treatment of other conditions, for example allergic conditions such as psoriasis and inflammatory diseases such as rheumatoid arthritis. In using a cyclopenta[g]quinazoline of the invention for such a purpose the compound will normally be administered at a dose within the range 5-25000, particularly 5-500, mg per square metre body area of the animal, i.e. approximately 0.1-500, particularly 0.1-10, mg/kg. Where desired, however, dosages outside this range may be employed. In general, for the treatment of an allergic condition such as psoriasis, topical administration of a cyclopenta[g]quinazoline of the invention is preferred. Thus, for example, for topical administration a daily dose in the range, for example, of 0.1 to 10 mg/kg may be used.

Compositions containing the quinazolines may be formulated in unit dosage form, i.e. in the form of discrete portions each comprising a unit dose, or a multiple or sub-multiple of a unit dose, for example as a tablet or capsule. Such a unit dosage form may, for example, contain an amount of the cyclopenta[g]quinazoline in the range of 1-250 or 1-500 mg.

The invention is illustrated by the following Examples.

EXAMPLE 1

Synthesis of CB300951 (2-CH$_2$OMe Derivative of CB300638)

5-Methoxyacetamidoindan

To a solution of 5-aminoindan (4.66 g, 35.0 mmol) in anhydrous DMF (26 ml) was slowly added methoxyacetyl chloride (5.70 g, 52.50 mmol) followed by pyridine (8.5 ml, 105.0 mmol). The red solution was stirred at room temperature for 3.5 hours under argon, then it was partitioned between ethyl acetate (200 ml) and 1N HCl (120 ml). The organic layer was washed with more 1N HCl (120 ml), brine (100 ml), dried (Na$_2$SO$_4$) and concentrated in vacuo. The residue was triturated with diethyl ether; the white precipitate was collected by filtration, washed with diethyl ether to afford the title compound (5.93 g, 83%), m.p. 104-105° C.; $^1$H-NMR (250 MHz, CDCl$_3$, TMS) 2.06 (m, 2H, 2-CH$_2$), 2.87 (m, 4H, 1-CH$_2$ and 3-CH$_2$), 3.50 (s, 3H, OCH$_3$), 4.00 (s, 2H, 2-CH$_2$OMe), 7.22 (m (overlap with CHCl$_3$ peak), 2H, 6-H, 7-H), 7.52 (s, 1H, 4-H), 8.18 (s, 1H, CONH); MS (ESI, m/z): 432 [(2M+Na)$^+$, 30%], 206[(M+H)$^+$, 100%]; Found C, 70.10; H, 7.38; N, 6.81; C$_{12}$H$_{15}$NO$_2$ requires C, 70.22; H, 7.37; N, 6.82%.

5-Methoxyacetamido-6-bromoindan

A mixture of 5-methoxyacetamidoindan (5.50 g, 0.027 mol) and glacial acetic acid (25 ml) was cooled in an ice-water bath (~10° C.). Bromine (1.5 ml, 0.029 mol) was then dropwise added over a 20 min period while the temperature was kept between 10-15° C. The reaction mixture was then stirred for a longer 1 hour and then it was poured into an ice-water bath (100 ml) with the aid of water (70 ml). The precipitate was collected by filtration, washed with plenty of water (150 ml) and dried in vacuo over P$_2$O$_5$ to afford the title compound (6.98 g, 91%), m.p. 84-86° C.; $^1$H-NMR (250 MHz, CDCl$_3$, TMS) 2.09 (m, 2H, 2-CH$_2$), 2.88 (m, 4H, 1-CH$_2$ and 3-CH$_2$), 3.55 (s, 3H, OCH$_3$), 4.04 (s, 2H, 2-CH$_2$OMe), 7.34, 8.22 (2×s, 2H, 4-H, 7-H), 8.83 (s, 1H, CONH);

MS (ESI, m/z): 284, 286 [(M+H)$^+$, 98%, 100%; Br isotopic pattern]; Found C, 50.62; H, 4.93; N, 4.92; Br, 28.05; C$_{12}$H$_{14}$BrNO$_2$ requires C, 50.72; H, 4.97; N, 4.93; Br, 28.12%.

5-Methoxyacetamido-6-bromoindan-1-one

To a solution of 5-methoxyacetamido-6-bromoindan (0.85 g, 3.0 mmol) in glacial acetic acid (7 ml) heated at 55° C. was dropwise added a solution of CrO$_3$ (1.2 g, 12.0 mmol) in aqueous glacial acetic acid, (7 ml, v/v 1:1) over a 15 min period. The reaction mixture was then stirred at this temperature for 45 min. The reaction mixture was cooled in an ice-bath, then propan-2-ol (4 ml) was added and the mixture was stirred at this temperature for 10 min before being concentrated in vacuo. The black residue was broken up with a spatula with the aid of water and then partitioned between water (50 ml) and ethyl-acetate (150 ml). The

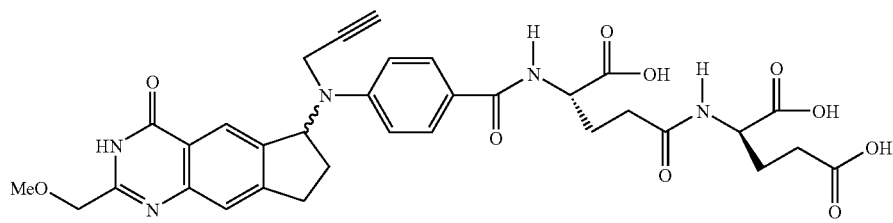

CB300951 aqueous layer was extracted with more ethyl acetate (2×40 ml), the combined extracts were dried ($Na_2SO_4$), and concentrated in vacuo to give an off white residue. Purification by column chromatography on elution with 5% ethyl acetate in dichloromethane afforded in order of elution:

a. 5-methoxyacetamido-6-bromoindan-1-one as a white solid which was further purified by trituration with ethyl acetate/hexanes (1:5, v/v): 0.50 g (55%), m.p. 162-163° C.; $^1$H-NMR (250 MHz, $CDCl_3$, TMS) 2.72 (m, 2H, 2-$CH_2$), 3.11 (m, 2H, 3-$CH_2$), 3.57 (s, 3H, $OCH_3$), 4.09 (s, 2H, 2-$CH_2$OMe), 7.95 (s, 1H) and 8.65 (s, 1H) (2H, 4-H, 7-H), 9.27 (s, 1H, CONH); MS (ESI, m/z) 298, 300 {$(M+H)^+$, 100%, 97% respectively, bromine isotopic pattern}; Found: C, 48.13; H, 3.99; N, 4.70; Br, 26.95; $C_{12}H_{12}BrNO_3$ requires C, 48.34; H, 4.06; N, 4.70; Br, 26.80%); and b. 5-acetamido-6-bromoindan-3-one as a solid which was further purified by trituration with ethyl acetate/hexanes (1:5, v/v): 0.026 g, (3%), m.p. 149-151° C.

$^1$H-NMR (250 MHz, $CDCl_3$, TMS) 2.71 (m, 2H, 2-$CH_2$), 3.01 (m, 2H, 1-$CH_2$), 3.56 (s, 3H, $OCH_3$), 4.08 (s, 2H, 2-$CH_2$OMe), 7.73 (s, 1H) and 8.71 (s, 1H) (2H, 4-H, 7-H), 8.97 (s, 1H, CONH); MS (ESI, m/z) 298, 300 {$(M+H)^+$, 100%, 98% respectively, bromine isotopic pattern}; Found: C, 47.95; H, 3.96; N, 4.59; Br, 26.63; $C_{12}H_{12}BrNO_3$ requires C, 48.34; H, 4.06; N, 4.70; Br, 26.80%).

tert-Butyl 4-[N-(5-methoxyacetamido-6-bromoindan-1-yl)amino]benzoate

Method A: To a flask containing 5-methoxyacetamido-6-bromoindan-1-one (0.357 g, 1.2 mmol), 4-toluenesulfonic acid monohydrate (0.015 g), and tert-butyl 4-aminobenzoate (0.289 g, 1.5 mmol) was added 1,2-dimethoxyethane (dried by distillation over $CaH_2$; 15 ml). An Aldrich azeotropic distillation apparatus containing molecular sieves (3A) was fitted to the reaction flask that was placed in an oil bath preheated to 115° C. The reaction mixture was stirred at this temperature for 3.5 hours under argon; then allowed to cool to room temperature, and a solution of sodium cyanoborohydride in tetrahydrofuran (1M; 1.55 ml, 1.55 mmol) was added followed immediately by acetic acid (0.044 ml). The black reaction mixture was stirred at room temperature for 1 hour under argon; then it was partitioned between ethyl acetate (150 ml) and saturated aqueous sodium bicarbonate (100 ml). The aqueous layer was extracted with more ethyl acetate (100 ml); the organic extracts were combined, washed with brine (100 ml), dried ($Na_2SO_4$), and concentrated in vacuo to leave a reddish residue. Purification by column chromatography, on elution with 35% ethyl acetate in petroleum ether (60-80° C.), afforded the desired product as a white solid: 0.175 g (31%).

Method B. To a nearly clear solution of 5-methoxyacetamido-6-bromoindan-1-one (0.300 g, 1.0 mmol) in anhydrous methanol (40 ml) was added tert-butyl 4-aminobenzoate (0.193 g, 1.0 mmol) followed by decaborane (0.044 g). The reaction mixture was stirred at room temperature for 24 hours before being concentrated in vacuo. Purification by column chromatography, on elution with 35% ethyl acetate in petroleum ether (60-80° C.), afforded a white solid that was further purified by reprecipitation from dichloromethane/hexane: 0.340 g, (72%) m.p, 152-153° C.; $^1$H-NMR (250 MHz, $CDCl_3$, TMS) 1.57 (s, 9H, C($CH_3$)$_3$), 1.93, 2.63 (2×m, 2H, indanyl 3-H), 2.97 (m, 2H, indanyl 3-H), 3.55 (s, 3H, $OCH_3$), 4.06 (s, 2H, $CH_2$OMe), 5.04 (t, J=6.50 Hz, 1H, 1-H), 6.64 (d, J=8.78 Hz, 2H, 3,5-H), 7.51, 8.33 (2×s, each 1H, indanyl 4-H, 7-H), 7.85 (d, J=8.75 Hz, 2,6-H), 8.93 (s, 1H, CONH); MS (ESI, m/z) 499, 497 {$(M+Na)^+$, bromine isotopic pattern}.

tert-Butyl 4-[N-(5-methoxyacetamido-6-cyanoindan-1-yl)amino]benzoate

To a solution of tert-butyl 4-[N-(5-methoxyacetamido-6-bromoindan-1-yl)amino]benzoate (0.714 g, 1.50 mol) in NMP (8 ml) [1-methyl-2-pyrrolidone] was added copper (I) cyanide (0.230 g, 2.55 mmol). The reaction mixture was placed in an oil-bath preheated to 140° C. and stirred at this temperature for 2 h. More copper (I) cyanide (0.100 g, 1.10 mmol) was then added and stirring was continued for a longer 3 hours. The reaction mixture was allowed to cool to room temperature, then poured into a mixture of aqueous ammonia (d=0.88, 7 ml) and ice (~20 ml) and the resulting brown mixture was stirred at room temperature for ~5 min. The brown solid was collected by filtration washed with plenty of water, then suspended in dichloromethane (100 ml). The mixture was stirred at room temperature for 10 min, dried ($Na_2SO_4$), and concentrated in vacuo. Purification by column chromatography, on elution with 35% ethyl acetate in hexane, afforded an off white solid that was reprecipitated from dichloromethane-ethyl acetate/hexane: 0.328 g, (52%) m.p. 163-164° C. $^1$H-NMR (250 MHz, DMSO-$d_6$, TMS) 1.50 (s, 9H, C($CH_3$)$_3$), 1.85, 2.58 (2×m, 2H, indanyl 2-H), 2.89 (m, 2H, indanyl 3-H), 3.41 (s, 3H, $OCH_3$), 4.05 (s, 2H, $CH_2$OMe), 5.06 (m, 1H, indanyl 1-H), 6.73 (d, J=8.82 Hz, 2H, 3,5-H), 6.82 (d, J=8.37 Hz, 1H, $N^{10}$—H), 7.59, 7.57 (2×s, each 1H, indanyl 4-H, 7-H), 7.66 (d, J=8.77 Hz, 2,6-H), 9.88 (s, 1H, CONH), MS (ESI, m/z) 444 {$(M+Na)^+$, 100%}; Found: C, 68.21; H, 6.47; N, 9.81; $C_{24}H_{27}N_3O_4$ requires C, 68.39; H, 6.46; N, 9.97%.

tert-Butyl 4-{N-[(6RS)-2-methoxymethyl-4-oxo-3,4,7,8-tetrahydro-6H-cyclopenta[g]quinazolin-6-yl]amino}benzoate A mixture of tert-butyl 4-[N-(5-methoxyacetamido-6-cyanoindan-1-yl)amino]benzoate (0.295 g, 0.70 mmol), ethanol (3.2 ml), and water (0.64 ml) was cooled in an ice-bath, then 30% aqueous $H_2O_2$ solution (0.60 ml) was added followed by granulated sodium hydroxide pellets (0.047 g, 1.19 mmol). The reaction mixture was stirred at ~0° C. for 10 min, then it was placed in an oil bath preheated to 55° C. and stirred at this temperature for 30 min. The reaction mixture was allowed to cool to room temperature, then the solvents were removed in vacuo and the residue was suspended in water (~15 ml). The pH of this mixture was adjusted to ~12 with 1N NaOH (got a clear solution), then to ~4 with 1N hydrochloric acid. The off white precipitate was collected by filtration, washed with water, dried in vacuo over $P_2O_5$: 0.262 g (89%), m.p. >122° C. (softens); $^1$H-NMR (250 MHz, DMSO-$d_6$, TMS) 1.50 (s, 9H, C($CH_3$)$_3$), 1.87, 2.56 (2×m, each 1H, 7-H), 3.00 (m, 2H, 8-H), 3.34 (s, 3H, $OCH_3$), 4.30 (s, 2H, 2-$CH_2$), 5.16 (m, 1H, 6-H), 6.78 (d, J=8.55 Hz, 2H, 3',5'-H), 6.89 (d, J=8.10, $N^{10}$—H), 7.52, 7.90 (2×s, each 1H, 5-H, 9-H), 7.67 (d, J=8.45 Hz, 2',6'-H), 12.12 (s, 1H, $N^3$—H); MS (ESI, m/z) 444 {$(M+Na)^+$, 40%}; Found: C, 67.19; H, 6.31; N, 9.69; $C_{24}H_{27}N_3O_4$ 0.5$H_2O$ requires C, 66.96; H, 6.50; N, 9.76%.

Dicobalthexacarbonyl Propargyl Alcohol Complex

This is a known compound (K.-D. Roth and U. Muller, *Tetrahedron Letters* 1993, 34, 2919) and in this study was prepared according to Nicholas' methodology (K. L. Salazar and K. M. Nicholas, *Tetrahedron* 2000, 56, 2211): To a round bottom flask charged with $Co_2(CO)_6$ (5.12 g, 15.0 mmol) under argon in a well ventilated hood was added anhydrous dichloromethane (170 ml) followed by a solution of propargyl alcohol (0.840 g, 15.0 mmol) in anhydrous dichloromethane (20 ml). The deep red reaction mixture was stirred at room temperature for 7 h under argon, then it was filtered through a thin layer of neutral alumina. The filtrate was concentrated in vacuo to give a red residue. Purification by column chromatography, on elution with 40% diethyl ether in hexane, afforded the desired product as a red solid 4.10 g (80%); $^1$H-NMR (250 MHz, CDCl$_3$, TMS) 1.83 (t, J=6.0 Hz, 1H, OH), 4.80 (d, J=6.0 Hz, 2H, CH$_2$), 6.08 (s, 1H, C—H).

(Propargyl)Co$_2$(CO)$_6$$^+$BF$_4$$^-$

This is a known compound (K.-D. Roth and U. Muller, *Tetrahedron Letters* 1993, 34, 2919) and in this study was prepared according to Nicholas' methodology (K. L. Salazar and K. M. Nicholas, *Tetrahedron* 2000, 56, 2211): To a round bottom flask charged with dicobalthexacarbonyl propargyl alcohol complex (1.60 g, 4.7 mmol) under argon was added (syringed via a septum) propionic acid (2.2 ml). The reaction mixture was cooled to −20° C. and then a solution of HBF$_4$ in diethyl ether (54% w/w, 2.05 ml) was slowly syringed into the reaction mixture via a septum. The reaction mixture was stirred at −20° C. for 40 min, then cooled diethyl ether (50 ml) was added. Trituration afforded a red precipitate that was collected by filtration, washed with plenty of dry diethyl ether and dried in vacuo over P$_2$O$_5$: 1.71 g (90%). This was immediately used in the next reaction without any further purification.

tert-Butyl 4-{N-[(6RS)-2-methoxymethyl-4-oxo-3,4,7,8-tetrahydro-6H-cyclopenta[g]quinazolin-6-yl]-N-(prop-2-ynyl)amino}benzoate To a round-bottomed flask containing the tetrafluoroborate salt (propargyl)Co$_2$(CO)$_6$$^+$BF$_4$$^-$ (0.271 g, 0.66 mmol) was added anhydrous dichloromethane (dried by distillation over P$_2$O$_5$; 22 ml). The nearly clear red dark solution was stirred at room temperature for few minutes under argon, then tert-butyl 4-{N-[(6RS)-2-methoxymethyl-4-oxo-3,4,7,8-tetrahydro-6H-cyclopenta[g]quinazolin-6-yl] amino}benzoate (0.215 g, 0.51 mmol) was added in one portion. Stirring was continued at this temperature for 5 min then diisopropylethylamine (0.18 ml, 1.04 mmol) was added and the reaction mixture was stirred at room temperature for 45 min under argon. The reaction mixture was partitioned between ethyl acetate (150 ml) and brine (60 ml). The aqueous layer was extracted with more ethyl acetate (2×50 ml). The combined extracts were washed with 10% aqueous citric acid (50 ml), brine (50 ml), dried (Na$_2$SO$_4$), and concentrated in vacuo. Purification by column chromatography, on elution with 40% ethyl acetate in dichloromethane, gave a red solid: 0.285 g (75%). To a solution of this complex (0.267 g, 0.36 mmol) in ethanol (60 ml) was added Fe(NO$_3$)$_3$.9H$_2$O (~8.0 g). The clear solution was stirred at room temperature for 10 min then a second portion of Fe(NO$_3$)$_3$.9H$_2$O (~4.0 g) was added. The reaction mixture was stirred at room temperature for a longer 5 min then a final portion of Fe(NO$_3$)$_3$.9H$_2$O (~5.0 g) was added; the nearly clear solution was turned into a dark red mixture. Stirring was continued at room temperature for an extra 25 min, then the reaction mixture was partitioned between ethyl acetate (150 ml) and dilute brine (700 ml). The aqueous layer was extracted with more ethyl acetate (2×70 ml), The combined organics were washed with brine (3×70 ml), dried (Na$_2$SO$_4$), and concentrated in vacuo. Purification by column chromatography, on elution with 2% methanol in dichloromethane, afforded a white solid which was reprecipitated from dichloromethane/hexane: 0.122 g (74%), m.p. 191-192° C.; $^1$H-NMR (250 MHz, DMSO-d$_6$, TMS) 1.51 (s, 9H, C(CH$_3$)$_3$), 2.23, 2.53 (m-obscured by DMSO peak) (2×m, each 1H, 7-H), 2.95-3.20 (m, 3H, C≡CH, 8-H), 3.34 (s (obscured by the H$_2$O peak), 3H, OCH$_3$), 3.96 (ABq, J=18.0 Hz, 2H, CH$_2$C≡C), 4.31 (s, 2H, 2-CH$_2$), 5.79 (t, J=7.0 Hz, 1H, 6-H), 7.02 (d, J=9.01 Hz, 2H, 3',5'-H), 7.58, 7.80 (2×s, each 1H, 5-H, 9-H), 7.76 (d, J=8.45 Hz, 2',6'-H), 12.17 (s, 1H, N$^3$—H); MS (ESI, m/z) 482 {(M+Na)$^+$, 10%}; Found: C, 70.32; H, 6.31; N, 9.09; C$_{27}$H$_{29}$N$_3$O$_4$ requires C, 70.57; H, 6.36; N, 9.14%.

4-{N-[(6RS)-2-Methoxymethyl-4-oxo-3,4,7,8-tetrahydro-6H-cyclopenta[g]quinazolin-6-yl]-N-(prop-2-ynyl)amino}benzoic acid A solution of tert-butyl 4-{N-[(6RS)-2-methoxymethyl-4-oxo-3,4,7,8-tetrahydro-6H-cyclopenta[g]quinazolin-6-yl]-N-(prop-2-ynyl)amino}benzoate (0.069 g, 0.15 mmol) in dichloromethane (1 ml) and trifluoroacetic acid (3 ml) was stirred at room temperature for 1 hour and 10 min, then the solvents were removed in vacuo. The residue was triturated with diethyl ether and the precipitate was collected by filtration, washed with diethyl ether and dried in vacuo over P$_2$O$_5$ to afford the title compound as the trifluoroacetate salt: 0.061 g, m.p. 225° C. (dec); $^1$H-NMR (250 MHz, DMSO-d$_6$, TMS) 2.23, 2.53 (obscured by DMSO peak) (2×m, each 1H, 7-H), 2.90-3.20 (m, 3H, C≡CH, 8-H), 3.34 (s (obscured by the H$_2$O peak), 3H, OCH$_3$), 3.97 (ABq, J=18.0 Hz, 2H, CH$_2$C≡C), 4.32 (s, 2H, 2-CH$_2$), 5.79 (t, J=8.1 Hz, 1H, 6-H), 7.03 (d, J=9.02 Hz, 2H, 3',5'-H), 7.58, (s, 1H, 9-H), 7.81 (m, 3H, 5-H, 2',6'-H), 12.17 (s, 1H, N$^3$—H); MS (ESI, m/z) 426 {(M+Na)$^+$, 25%}, 404 {(M+H)$^+$, 70%}.

Tri-tert-butyl N-{N-{4-[N-((6RS)-2-methoxymethyl-4-oxo-3,4,7,8-tetrahydro-6H-cyclopenta[g] quinazolin-6-yl)-N-(prop-2-ynyl)amino]benzoyl}-L-γ-glutamyl}-D-glutamate To a mixture of 4-{N-[(6RS)-2-methoxymethyl-4-oxo-3,4,7,8-tetrahydro-6H-cyclopenta[g]quinazolin-6-yl]-N-(prop-2-ynyl)amino}benzoic acid trifluoroacetate salt (0.056 g, ~0.14 mmol), tri-tert-butyl L-γ-glutamyl-D-glutamate (0.090 g, 0.20 mmol) and anhydrous DMF (2.5 ml) was added diethyl cyanophosphonate (0.050 g, 0.31 mmol) followed by triethylamine (0.035 g, 0.35 mmol). The clear solution was stirred at room temperature for 2 hours, then it was partitioned between ethyl acetate (150 ml) and water (80 ml). The aqueous layer was extracted with ethyl acetate (2×70 ml). The combined organics were washed with 10% aqueous citric acid (2×40 ml), saturated sodium bicarbonate solution (100 ml) and brine (100 ml), dried (Na$_2$SO$_4$), and concentrated in vacuo. Purification by column chromatography, on elution with 1.5% methanol in ethyl acetate, afforded a white solid that was further purified by trituration with hexane with the aid of some dichloromethane: 0.072 g (64%); m.p. >120° C.; $^1$H-NMR (250 MHz, DMSO-d$_6$, TMS) 1.38, 1.39, 1.41 (3×s, 27H, 3×C (CH$_3$)$_3$), 1.60-2.35 (m, 9H, 2×β-CH$_2$, 2×γ-CH$_2$, 7-H), 2.52 (m obscured by DMSO peak, 1H, 7-H), 2.90-3.25 (m, 3H, C≡CH, 8-H), 3.97 (ABq, J=17.0 Hz, 2H, CH$_2$C≡C), 4.08, 4.12 (2×m, 2H, 2×α-CH), 4.32 (s, 2H, 2-CH$_2$), 5.77 (t, J=7.50 Hz, 1H, 6-H), 7.02 (d, J=8.85 Hz, 2H, 3',5'-H), 7.58 (s, 1H, 9-H), 7.80 (d, J=9.0 z, 2H, 2',6'-H), 7.82 (s, 1H, 5-H), 8.17 (d, J=8.12 Hz, 1H, CONH), 8.36 (d, J=7.00 Hz, 1H, CONH), 12.16 (s, 1H, N$^3$—H); MS (ESI, m/z) 852 {(M+

Na)+, 20%}, 830 {(M+H)+, 100%}, Found C, 64.71; H, 7.21; N, 8.27. $C_{45}H_{59}N_5O_{10}$ requires C, 65.12; H, 7.17; N, 8.44%.

N-{N-{4-[N-(6RS)-2-Methoxymethyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid A solution of tri-tert-butyl N-{N-{4-[N-((6RS)-2-methoxymethyl-4-oxo-3,4,7,8-tetrahydro-6H-cyclopenta[g]quinazolin-6-yl)-N-(prop-2-ynyl)amino]-benzoyl}-L-γ-glutamyl}-D-glutamate (0.056 g, 0.07 mmol) in trifluoroacetic acid (4.5 ml) was stirred at room temperature for 1 hour and 10 min with protection from the light. The solvent was then removed in vacuo and the residue was suspended in water (4 ml). The pH was adjusted to ~10 with 1N NaOH, then to ~4 with 1N hydrochloric acid. The white precipitate was collected by filtration and dried in vacuo over $P_2O_5$: 0.020 g (45%), m.p. 150-155° C. (softens), $^1$H-NMR (250 MHz, DMSO-$d_6$, TMS) 1.60-2.30 (m, 9H, 2×β-$CH_2$, 2×γ-$CH_2$, 7-H), 2.52 (m obscured by DMSO peak, 1H, 7-H), 2.90-3.25 (m, 3H, C≡CH, 8-H), 3.36 (s, 3H, $OCH_3$), 3.97 (ABq, J=17.0 Hz, 2H, $CH_2$C≡C), 4.20, 4.34 (2×m, 2H, 2×α-CH), 4.32 (s, 2H, 2-$CH_2$), 5.77 (t, J=8.02 Hz, 1H, 6-H), 7.02 (d, J=8.85 Hz, 2H, 3',5-H), 7.58 (s, 1H, 9-H), 7.81 (d, J=9.0 z, 2H, 2',6'-H), 7.83 (s, 1H, 5-H), 8.14 (d, J=8.12 Hz, 1H, CONH), 8.33 (d, J=7.78 Hz, 1H, CONH), 12.10 (s, 1H, $N^3$—H); MS (ESI, m/z) 662 {(M+H)+, 100%}.

EXAMPLE 2

Synthesis of CB300945 (2-CH$_2$OH Derivative of CB300638)

The insoluble brown solid was removed by filtration and the resulting solution was acidified to pH 5 with 1M hydrochloric acid. The precipitate was collected by filtration, washed with acidified water and dried in vacuo over $P_2O_5$ to yield the product as a pale yellow solid (1.17 g, 58%); m.p. 205-210° C.; $^1$H NMR (DMSO-$d_6$) δ 2.07 (quin, J=7.4 Hz, 2H, 7-H), 2.98 (q, J=6.95 Hz, 4H, 6-H and 8-H), 4.38 (s, 2H, 2-$CH_2$), 7.46 (s, 1H, 9-H), 7.92 (s, 1H, 5-H); MS (FAB-m/z): Found 217 [(M+H)+, 100%]; HRMS: measured 217.0977; calculated for $C_{12}H_{13}N_2O_2$ (M+H)+: 217.0977; Found C, 64.01; H, 5.23; N, 12.34. $C_{12}H_{13}N_2O_2$·½$H_2O$ requires C, 63.93; H, 5.77; N, 12.43%.

2-2,2-Dimethylpropionyloxymethyl)-3,4,7,8-tetrahydro-6H-cyclopenta[g]quinazolin-4-one 2-Hydroxymethyl-3,4,7,8-tetrahydro-6H-cyclopenta[g]quinazolin-4-one (1.0 g, 4.6 mmol), triethylamine (0.77 ml, 5.6 mmol), DMAP (50 mg, 0.4 mmol) and anhydrous $CH_2Cl_2$ (50 ml) were mixed in a flask under argon. Pivalic anhydride (1.2 ml, 6.0 mmol) was added dropwise and the suspension stirred at room temperature under argon for 5 h. The solvent was removed in vacuo and the residue partitioned between EtOAc (100 ml) and saturated aqueous $NaHCO_3$ (100 ml). The organic extract was washed with saturated aqueous $NaHCO_3$ (70 ml), water (70 ml), brine (70 ml), dried ($Na_2SO_4$) and the solvent removed in vacuo. The residue was triturated with hexane (60 ml) and the product collected by filtration as a yellow solid (1.21 g, 87%); m.p. 185-190° C.; $^1$H-NMR (DMSO-$d_6$) δ 1.22 (s, 9H, $CMe_3$), 2.07 (quin, J=7.4 Hz, 2H, 7-H), 2.98 (q, J=5.72 Hz, 4H, 6-H and 8-H), 4.94 (s, 2H, 2-$CH_2$), 7.42 (s, 1H, 9-H), 7.92 (s, 1H, 5-H), 12.20 (br, 1H, NH); MS (FAB, m/z): Found 301 [(M+H)+, 100%]; HRMS: measured 301.1539; calculated

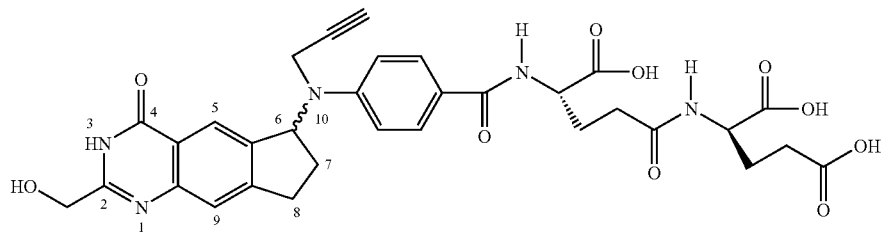

CB300945

2-Hydroxymethyl-3,4,7,8-tetrahydro-6H-cyclopenta[g]quinazolin-4-one

A solution of caesiun acetate (14.4 g, 75.2 mmol) in dry DMF (40 ml) was heated to 60° C. under argon for 30 min. The mixture was cooled to 40° C. and a suspension of 2-chloromethyl-3,4,7,8-tetrahydro-6H-cyclopenta[g]quinazolin-4-one (L. Skelton, V. Bavetsias, A. Jackman, WO 00/050417-A1; 2.2 g, 9.4 mmol) in dry DMF (60 ml) was added via a cannula. The mixture was heated to 80° C. under argon for 16 h. The mixture was cooled to room temperature and the solvent was removed in vacuo. The residue was suspended in water (50 ml) and MeOH (20 ml). The pH was adjusted to 12.5 with 1M sodium hydroxide solution and the brown suspension was stirred for 2 h at room temperature.

for $C_{17}H_{21}N_2O_3$ (M+H)+: 301.1552; Found C, 67.65; H, 6.54; N, 9.54. $C_{17}H_{20}N_2O_3$ requires C, 67.98; H, 6.71; N, 9.33%.

2-(2,2-Dimethylpropionyloxymethyl)-3,4,7,8-tetrahydro-6H-cyclopenta-[g]quinazolin-4,6-dione and 2-(2,2-Dimethylpropionyloxymethyl)-3,4,7,8-tetrahydro-6H-cyclopenta[g]quinazolin-4,8-dione To a stirred solution of $(Ph_3SiO)_2CrO_2$ (L. M. Baker and W. L. Carrick, J. Org. Chem. 1970, 35, 774) (10.6 mg, 0.017 mmol) in $CH_2Cl_2$ (5 ml) was added sequentially aqueous 70% tert-butyl hydroperoxide (0.18 ml, 1.3 mmol) and 2-(2,2-dimethylpropionyloxymethyl)-3,4,7,8-tetrahydro-6H-cyclopenta[g]quinazolin-4-one (0.1 g, 0.33 mmol). The mixture was stirred at room temperature with protection from the light for 24 h. The solvents were removed in vacuo and the residue purified by column chromatography (20 g of silica gel) eluting with a gradient of 10-30% EtOAc in $CHCl_3$ to yield 2-(2,2-dimethylpropionyloxymethyl)-3,4,7,8-tetrahydro-6H-cyclopenta[g]quinazolin-4,6-dione as a white solid (47 mg, 45%); m.p. 185-190° C.; $^1$H-NMR (DMSO-$d_6$) δ 1.23 (s, 9H, $CMe_3$), 2.72 (m, 2H, 7-H), 3.25 (m, 2H, 8-H), 5.00 (s, 2H, 2-$CH_2$), 7.70 (s, 1H, 9-H), 8.29 (s, 1H, 5-H), 12.20 (br, 1H, NH); MS (FAB, m/z): Found 315 [(M+H)$^+$, 100%], 337 [(M+Na)$^+$, 75%]; HRMS: measured 315.1360; calculated for $C_{17}H_{19}N_2O_4$ (M+H)$^+$: 315.1345; Found C, 64.188; H, 5.72; N, 8.81. $C_{11}H_{18}N_2O_4$·0.2$H_2O$ requires C, 64.23; H, 5.79; N, 8.82%.

2-2,2-Dimethylpropionyloxymethyl)-3,4,7,8-tetrahydro-6H-cyclopenta[g]-quinazolin-4,8-dione, $^1$H-NMR (DMSO-$d_6$) δ 1.23 (s, 9H, $CMe_3$), 2.76 (m, 2H, 7-H), 3.26 (m, 2H, 8-H), 4.98 (s, 2H, 2-$CH_2$), 7.72 (s, 1H, 9-H), 8.29 (s, 1H, 5-H), 12.3 (br, 1H, NH).

tert-Butyl 4-[N-((6RS)-2-(2,2-dimethylpropionyloxymethyl)-4-oxo-3,4,7,8-tetrahydro-6H-cyclopenta[g]quinazolin-6-yl)amino]benzoate A suspension of 2-(2,2-dimethylpropionyloxymethyl)-3,4,7,8-tetrahydro-6H-cyclopenta[g]quinazolin-4,6-dione (0.47 g, 1.50 mmol) in anhydrous methanol (33 ml) and anhydrous $CH_2Cl_2$ (5 ml) was treated with tert-butyl 4-aminobenzoate (0.34 g, 1.78 mmol) followed by decaborane (0.07 g, 0.58 mmol) and the mixture stirred at room temperature under argon for 18 h. The solvent was removed in vacuo and the residue purified by column chromatography (50 g of silica gel) eluting with 30% ethyl acetate in $CH_2Cl_2$ to yield the desired product as a white solid (0.43 g, 58%); m.p. 231° C.; $^1$H-NMR (CDCl$_3$) δ 1.26 (s, 9H, $CMe_3$), 1.58 (s, 9H, $CO_2CMe_3$), 2.00 (m, 1H, 7-H), 2.72 (m, 1H, 7-H), 3.08 (m, 2H, 8-H), 5.10 (s, 2H, 2-$CH_2$), 5.15 (m, 1H, 6-H), 6.67 (d, J=8.8 Hz, 2H, 3'-H, 5'-H), 7.58 (s, 1H, 9-H), 7.87 (d, J=8.8 Hz, 2H, 2'-H, 6'-H), 8.24 (s, 1H, 5-H); MS (FAB, m/z): Found 491 [(M+H)$^+$, 25%], 514 [(M+Na)$^+$, 100%]; Found C, 68.37; H, 6.86; N, 8.35. $C_{28}H_{33}N_3O_5$ requires C, 68.41; H, 6.77; N, 8.55%.

tert-Butyl 4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)amino]benzoate A suspension of (propargyl)$Co_2(CO)_6^+BF_4^-$ (213 mg, 0.52 mmol) in anhydous $CH_2Cl_2$ (25 ml) was treated with tert-butyl 4[-N-((6RS)-2-(2,2-dimethyl-propionyloxymethyl)-4-oxo-3,4,7,8-tetrahydro-6H-cyclopenta[g]quinazolin-6-yl)amino]benzoate (200 mg, 0.41 mmol) and the red solution stirred at room temperature under argon for 15 minutes. Diisopropylethylamine (0.15 ml, 0.86 mmol) was added and the mixture stirred at room temperature under argon for 1 h. The mixture was partitioned between ethyl acetate (30 ml) and brine (30 ml). The organic extract was dried ($Na_2SO_4$) and the solvent removed in vacuo. The residue was purified by column chromatography (20 g of silica gel) eluting with a gradient of 0-10% ethyl acetate in $CH_2Cl_2$ to yield the complex as a red oil (191 mg, 58%), $^1$H-NMR (CDCl$_3$) δ 1.26 (s, 9H, $CMe_3$), 1.59 (s, 9H, $CO_2CMe_3$), 2.31 (m, 1H, 7-H), 2.62 (m, 1H, 7-H), 3.13 (m, 2H, 8-H), 4.57 (AB system, J=16.9 Hz, 2H, propargyl $CH_2$), 5.09 (s, 2H, 2-$CH_2$), 5.63 (t, J=8.3, 1H, 6-H), 5.98 (s, 1H, propargyl CH), 6.91 (d, J=8.9 Hz, 2H, 3'-H, 5'-H), 7.61 (s, 1H, 9-H), 7.90 (d, J=8.9 Hz, 2H, 2'-H, 6'-H), 8.14 (s, 1H, 5-H), 10.25 (br s, 1H).

A solution of this complex (186 mg, 0.23 mmol) in ethanol (30 ml) was treated with Fe(NO$_3$)$_3$·9$H_2O$ (1.1 g) and the solution stirred at room temperature for 2 h. The solution was partitioned between ethyl acetate (30 ml) and water (30 ml). The organic extract was washed with brine (30 ml), dried ($Na_2SO_4$) and the solvent removed in vacuo. The residue was purified by column chromatography (20 g of silica gel) eluting with 10% ethyl acetate in $CH_2Cl_2$ to yield the desired product as a white solid (94 mg, 78%); m.p. 134° C.; $^1$H-NMR (CDCl$_3$) δ 1.32 (s, 9H, $CMe_3$), 1.61 (s, 9H, $CO_2CMe_3$), 2.23 (s, 1H, propargyl CH), 2.38 (m, 1H, 7-H), 2.62 (m, 1H, 7-H), 3.07 (m, 1H, 8-H), 3.25 (m, 1H, 8-H), 3.94 (AB system, J=18.6 Hz, 2H, propargyl $CH_2$), 5.12 (s, 2H, 2-$CH_2$), 5.68 (t, J=8.2 Hz, 1H, 6-H), 6.99 (d, J=9.1 Hz, 2H, 3'-H, 5'-H), 7.63 (s, 1H, 9-H), 7.95 (d, J=9.0 Hz, 2H, 2'-H, 6'-H), 8.16 (s, 1H, 5-H), 9.55 (br s, 1H); MS (ESI, m/z) 552 {(M+Na)$^+$, 100%}, 530 {(M+H)$^+$, 20%}; Found C, 70.14; H, 6.80; N, 7.73. $C_{31}H_{35}N_3O_5$ requires C, 70.30; H, 6.66; N, 7.93%.

4-[N-((6RS)-2-(2,2-Dimethylpropionyloxymethyl)-4-oxo-3,4,7,8-tetrahydro-6H-cyclopenta[g]quinazolin-6-yl)-N-(prop-2-ynyl)amino]benzoic acid A solution of tert-butyl 4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)amino]-benzoate (80 mg, 0.15 mmol) in trifluoroacetic acid (5 ml) was stirred at room temperature with protection from the light for 1.5 h. The solvent was removed in vacuo and the residue triturated with 1:1 diethyl ether and hexane to yield the desired product as a white solid (81 mg, TFA salt); m.p. 133° C., $^1$H-NMR (DMSO-d6) δ 1.23 (s, 9H, $CO_2CMe_3$), 2.22 (m, 1H, 7-H), 2.50 (m, 1H, 7-H), 3.03 (m, 2H, 8-H), 3.14 (s, 1H, propargyl CH), 3.97 (AB system, J=18.8 Hz, 2H, propargyl $CH_2$), 4.95 (s, 2H, 2-$CH_2$), 5.79 (t, J=8.6 Hz, 1H, 6-H), 7.03 (d, J=9.0 Hz, 2H, 3'-H, 5'-H), 7.51 (s, 1H, 9-H), 7.81 (d, J=6.6 Hz, 2H, 2'-H, 6'-H), 7.83 (s, 1H, 5-H).

Tri-tert-butyl N-{N-{4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)amino]benzoyl}-L-γ-glutamyl}-D-glutamate A solution of 4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)amino]benzoic acid (80 mg, 0.15 mmol) in anhydrous dimethylformamide (7 ml) was treated with tri-tert butyl-L-γ-glutamyl-D-glutamate (150 mg, 0.33 mmol), diethyl cyanophosphonate (0.06 ml, 0.40 mmol) and triethylamine (0.06 ml, 0.40 mmol). The solution was stirred at room temperature under argon with protection from the light for 2.5 h. The solution was partitioned between ethyl acetate (25 ml) and water (25 ml). The aqueous layer was extracted with ethyl acetate (2×20 ml). The combined organic extracts were washed with 10% aqueous citric acid (2×30 ml), saturated aqueous NaHCO$_3$ (30 ml), dilute brine (30 ml), dried ($Na_2SO_4$) and the solvent removed in vacuo. The residue was purified by column chromatography (30 g of silica gel) eluting with 40% ethyl acetate in $CH_2Cl_2$ to yield the desired product as a white solid (94 mg, 62%); m.p. 109° C.; $^1$H-NMR (CDCl$_3$) δ 1.29 (s, 9H, —$COCMe_3$), 1.43 (s, 9H, $COOCMe_3$), 1.47 (s, 9H, $COOCMe_3$), 1.48 (s, 9H, $COOCMe_3$), 1.60-2.10 (m, 5H, 2×glu β-$CH_2$, 7-CH), 2.21 (s, 1H, propargyl CH), 2.22-2.50 (m, 4H, 2×glu γ-$CH_2$), 2.59 (m, 1H, 7-H), 3.08 (m, 1H, 8-H), 3.20 (m, 1H, 8-H), 3.92 (AB system, J=19.0 Hz, 2H, propargyl CH$_2$), 4.48, 4.76 (2×m, 2H, 2×glu α-CH), 5.12 (s, 2H, 2-CH$_2$), 5.64 (t, J=8.1 Hz, 1H, 6-H), 6.99 (d, J=8.8 Hz, 2H, 3'-H, 5'-H), 7.07 (m, 2H, 2×CONH), 7.64 (s, 1H, 9-H), 7.80 (d, J=8.8 Hz, 2H, 2'-H, 6'-H), 8.13 (s, 1H, 5-H); MS (ESI, m/z) 922 {(M+Na)$^+$, 100%}, 900 {(M+H)$^+$, 40%}, Found C, 64.85; H, 7.23; N, 7.33. C$_{49}$H$_{65}$N$_5$O$_{11}$.0.5H$_2$O requires C, 64.76; H, 7.27; N, 7.71%.

N-{N-{4-[N-((6RS)-2-Hydroxymethyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid Tri-tert-butyl N-{N-{4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)amino]-benzoyl}-L-γ-glutamyl}-D-glutamate (80 mg, 0.09 mmol) was dissolved in trifluoroacetic acid (5 ml) and stirred at room temperature with protection from the light for 1 h. The solvent was removed in vacuo and the residue dissolved in methanol (3 ml) and water (3 ml). The pH of the solution was adjusted to pH 12 with 1M sodium hydroxide solution and stirred at room temperature for 6 h. The solution was acidified to pH 4 with 1M hydrochloric acid and cooled to 0° C. The precipitate was collected by filtration and dried under vacuum over P$_2$O$_5$ to yield the desired product as a pale brown solid (27 mg, 47%); m.p. 172° C.; $^1$H-NMR (DMSO-d$_6$) δ 1.60-2.10 (m, 5H, 2×glu β-CH$_2$, 7-CH), 2.15-2.40 (m, 5H, 2×glu γ-CH$_2$, 7-H), 2.99 (m, 1H, 8-H), 3.12 (s, 1H, propargyl CH), 3.16 (m, 1H, 8-H), 3.98 (AB system, J=19.9 Hz, 2H, propargyl CH$_2$), 4.18, 4.30 (2×m, 2H, 2×glu α-CH), 4.36 (s, 2H, 2-CH$_2$), 5.58 (br s, 1H, —OH), 5.77 (t, J=7.9 Hz, 1H, 6-H), 7.01 (d, J=8.9 Hz, 2H, 3'-H, 5'-H), 7.54 (s, 1H, 9-H), 7.80 (d, J=8.5 Hz, 2H, 2'-H, 6'-H), 7.82 (s, 1H, 5-H), 8.15 (d, J=7.5 Hz, 1H), 8.35 (d, J=7.2 Hz, 1H) (2×CONH); MS (ESI, m/z) 670 {(M+Na)$^+$, 45%}, 648 {(M+H)$^+$, 100%}; HRMS: measured 648.2313; calculated for C$_{32}$H$_{35}$N$_5$O$_{10}$ (M+H)$^+$: 648.2306.

EXAMPLE 3

Synthesis of CB300960 (N-methyl Derivative of CB300945)

6H-cyclopenta[g]quinazolin-6-yl]-N-(prop-2-ynyl)amino}benzoate (0.150 g, 0.28 mmol) in dichloromethane (2 ml) and trifluoroacetic acid (6 ml) was stirred at room temperature for 1 hour. The solvents were then removed in vacuo, and the residue was suspended in methanol (3 ml) and water (5 ml). The pH was adjusted to ~10 with 1N NaOH (1.1 ml), and the mixture was stirred at room temperature for 4 hours. The reaction mixture was diluted with water (5 ml) and the pH was adjusted to ~5 with 1N HCl. The solid was then collected by filtration, but $^1$H-NMR indicated no complete removal of the pivaloyl group. This solid was suspended into the filtrate and then 1N NaOH (0.9 ml, 0.9 mmol) was added (pH ~12). The mixture was stirred at room temperature for 3.5 hours, then more 1N NaOH (0.2 ml) was added, and the mixture was stirred at room temperature for a further 0.5 hours. The pH was then adjusted to ~5.0 with 1N HCl. The off-white precipitate was collected by filtration, washed with water, and dried in vacuo over P$_2$O$_5$: 0.086 g, (79%); $^1$H-NMR (250 MHz, DMSO-d$_6$, TMS) 2.22 (m, 1H 7-CH), 2.90-3.30 (m, 3H, C≡CH, 8-H), 3.97 (ABq, J=18.6 Hz, 2H, CH$_2$C≡C), 4.37 (d, J=6.1 Hz, 2H, 2-CH$_2$), 5.56 (t, 1H, CH$_2$OH), 5.78 (t, J=7.51 Hz, 1H, 6-H), 7.03 (d, J=8.9 Hz, 2H, 3',5'-H), 7.55 (s, 1H, 9-H), 7.82 (m, 3H, 2',6'-H, 5-H), MS (ESI, m/z) 779 {(2M+H)$^+$, 100%}, 390 {(M+H)$^+$, 60%}.

Method B: A solution of tert-butyl 4-{N-[(6RS)-2-hydroxymethyl-4-oxo-3,4,7,8-tetrahydro-6H-cyclopenta[g]quinazolin-6-yl]-N-(prop-2-ynyl)amino}-benzoate (0.050 g, 0.11 mmol) in dichloromethane (1 ml) and trifluoroacetic acid (2.4 ml) was stirred at room temperature for 1 hour. The solvents were then removed in vacuo, and the residue was triturated with diethyl ether. The off-white precipitate was collected by filtration, and washed with ether to obtain the desired product as the trifluoroacetate salt: 0.044 g.

Tri-tert-butyl N-{N-{4-[N-((6RS)-2-hydroxymethyl-4-oxo-3,4,7,8-tetrahydro-6H-cyclopenta[g]quinazolin-6-yl)-N-(prop-2-ynyl)amino]benzoyl}-L-γ-glutamyl}-N-methyl-L-glutamate To a mixture of 4-{N-[(6RS)-2-hydroxymethyl-4-oxo-3,4,7,8-tetrahydro-6H-cyclopenta[g]quinazolin-6-yl]-N-(prop-2-ynyl)amino}benzoic acid (0.075 g, ~0.19 mmol), tri-tert-butyl L-γ-glutamyl-N-methyl-L-glutamate (V.

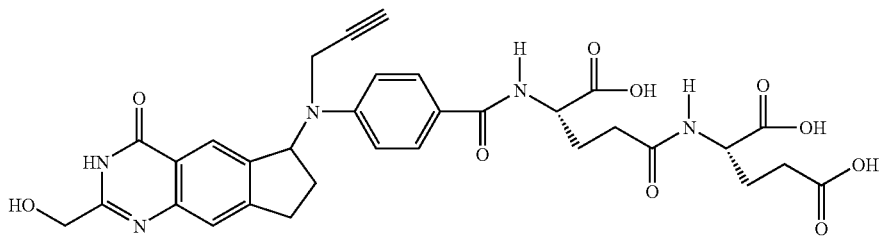

CB300960

4-{N-[(6RS)-2-Hydroxymethyl-4-oxo-3,4,7,8-tetrahydro-6H-cyclopenta[g]quinazolin-6-yl]-N-(prop-2-ynyl)amino}benzoic acid Method A: A solution of tert-butyl 4-{N-[(6RS)-2-(2,2-dimethylpropionyloxymethyl)-4-oxo-3,4,7,8-tetrahydro- Bavetsias et al., J. Med. Chem., 1997, 40, 1495-1510, 0.110 g, 0.24 mmol), and anhydrous DMF (2.0 ml) was added diethyl cyanophosphonate (0.036 g, 0.22 mmol) with the aid of anhydrous DMF (0.2 ml) followed by triethylamine (0.022 g, 0.22 mmol). The clear solution was stirred at room temperature for 1.5 hours, then it was partitioned between ethyl acetate (50 ml) and brine (40 ml). The aqueous layer was extracted with more ethyl acetate (2×50 ml). The combined organics were washed with 10% aqueous citric acid (40 ml), saturated sodium bicarbonate solution (40 ml), and brine (40 ml), dried ($Na_2SO_4$), and concentrated in vacuo. Purification by column chromatography, on elution with a gradient of methanol in dichloromethane (0 to 6%), afforded an off-white solid that was further purified by trituration with hexane/dichloromethane/diethyl ether: 0.062 g (40%); mp 116-120° C. (softens); $^1$H-NMR (250 MHz, DMSO-$d_6$, TMS) 1.36, 1.37, 1.38, 1.41 (4×s, 27H, 3×C($CH_3$)$_3$), 1.70-2.35 (m) and 2.50 (m obscured by DMSO peak) (10H, 2×β-$CH_2$, 2-γ×$CH_2$, 7-$CH_2$), 2.63, 2.82 (2×s, 3H, CONMe), 2.90-3.25 (m, 3H, C≡CH, 8-H), 3.97 (ABq, J=17.6 Hz, 2H, $CH_2$C≡C), 4.32 (m, 1H, glu α-CH), 4.38 (d, J=6.1 Hz, 2H, 2-$CH_2$), 4.50, 4.82 (2×dd, 1H, Meglu α-CH), 5.56 (t, J=6.9 Hz, 1H, $CH_2$OH), 5.78 (t, J=7.10 Hz, 1H, 6-H), 7.02 (d, J=8.6 Hz, 2H, 3',5'-H), 7.55 (s, 1H, 9-H), 7.78 (d, J=8.9 Hz, 2H, 2',6'-H), 7.82 (s, 1H, 5-H), 8.32 (m, 1H, CONH), 11.81 (s, 1H, $N^3$—H); MS (EST, m/z) 830{(M+H)$^+$, 100%}.

N-{N-{4-[N-((6RS)-2-hydroxymethyl-4-oxo-3,4,7, 8-tetrahydro-6H-cyclopenta[g]quinazolin-6-yl)-N-(prop-2-ytyl)amino]benzyl}-L-γ-glutamyl}-N-methyl-L-glutamic acid A solution of tri-tert-butyl N-{N-{4-[N-((6RS)-2-hydroxymethyl-4-oxo-3,4,7,8-tetrahydro-6H-cyclopenta[g] quinazolin-6-yl)-N-(prop-2-ynyl)amino]benzoyl}-L-γ-glutamyl}-N-methyl-L-glutamate (0.060 g, 0.07 mmol) in trifluoroacetic acid (3.5 ml) was stirred at room temperature for 1 hour and 10 min with protection from the light. The solvent was then removed in vacuo and the residue was suspended in water (6 ml). The pH was adjusted to ~10 with 1N NaOH, then to ~4 with 1N hydrochloric acid. The white precipitate was collected by filtration, and dried in vacuo over $P_2O_5$: 0.035 g (77%), mp >165° C. (dec); $^1$H-NMR (250 MHz, DMSO-$d_6$, TMS) 1.80-2.35 (m) and 2.50 (m obscured by DMSO peak) (10H, 2×β-$CH_2$, 2×γ-$CH_2$, 7-$CH_2$), 2.66, 2.83 (2×s, 3H, CONMe), 2.90-3.25 (m, 3H, C≡CH, 8-H), 3.97 (ABq, J=18.4 Hz, 2H, $CH_2$C≡C), 4.32 (m obscured, 1H, glu α-CH), 4.38 (d, J=5.6 Hz, 2H, 2-$CH_2$), 4.55, 4.91 (2×dd, J=10.0, 4.5 Hz, 1H, Meglu α-CH), 5.56 (poorly resolved t, 1H, $CH_2$OH), 5.77 (t, J=8.06 Hz, 1H, 6-H), 7.02 (d, J=7.8 Hz, 2H, 3',5'-H), 7.55 (s, 1H, 9-H), 7.81 (d, J=10.1 Hz, 3H, 2',6'-H, 5-H), 8.32 (m, 1H, CONH), 11.82 (s, 1H, $N^3$—H); MS (ESI, m/z) 662 {(M+H)$^+$, 100%}; Found: C, 57.52; H, 5.52, N, 10.17; $C_{33}H_{35}N_5O_{10}$ 1.5 $H_2O$ requires: C, 57.55; H, 5.56; N, 10.17%.

EXAMPLE 4

In vitro Evaluation

CB300945, the (RS)-C2-$CH_2$OH analogue of the known cyclopenta[g]-quinazoline, CB300638 was synthesised as in Example 1. In addition, the C2-$NH_2$ was made as a comparative example. The activity of this new series of cyclopenta[g]quinazolines with C2-$CH_3$ (RS-CB300638), C2-$CH_2$OH (RS-CB300945) and C2-$NH_2$ (RS-CB300944) substitutions were compared with three other series of quinazoline derivatives in mouse L1210-FBP cells and human tumour cell lines co-expressing the RFC and α-FR. The human A431-FBP cell line was transfected with the α-FR and sensitivity compared with the A431 cell line. Human nasopharengeal KB cells constitutively overexpress this receptor (see Bagnoli et al. *Oncogene*, 19, 4754-4763, 2000).

In the quinazoline series, the C2-$CH_2$OH analogues were found to have lower affinities for the α-FR of L1210-FBP cells (0.21 to 0.29) than the 2-$CH_3$ (0.37 to 0.54) and particularly the 2-$NH_2$ (1.3 to 1.7) counterparts. In the cyclopenta[g]quinazoline series the C2-$CH_3$ analogue (CB300639) had a relative binding affinity of 0.57. However, unexpectedly the C2-$CH_2$OH analogue (CB300945) had a higher affinity than predicted (0.71) and the C2-$NH_2$ analogue (CB300944) had one lower than predicted (0.57). Thus in the cyclopenta[g]quinazoline series C2-substitution did not markedly affect binding to the α-FR. A similar pattern of binding was noted for α-FR expressed by A431-FBP cells (data not shown).

A431-FBP and KB cells were highly sensitive to the C2-$CH_3$ cyclopenta[g]quinazoline with a L-glu-γ-D-glu ligand (S or RS-CB300638). However, very little activity of the C2-$NH_2$ analogue (PS-CB300944) could be attributed to α-FR mediated uptake into either of these cell lines (Tables 13). On the other hand the C2-$CH_2$OH analogue (RS-CB300945) was highly potent in A431-FBP and KB cells and more highly selective for these cells compared with A431 cells, than RS-CB300638.

Tables 4 and 5 show the structures of the compounds tested.

EXAMPLE 5

Formulation

The following illustrate representative pharmaceutical dosage forms containing a cyclopenta[g]quinazoline of formula (I), particularly in pharmaceutically acceptable salt form, for therapeutic or prophylactic use in humans:

| (a) Tablet I | mg/tablet |
|---|---|
| Cyclopenta[g]quinazoline salt | 100 |
| Lactose Ph.Eur. | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Cyclopenta[g]quinazoline salt | 50 |
| Lactose Ph.Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Cyclopenta[g]quinazoline salt | 1.0 |
| Lactose Ph.Eur. | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Cyclopenta[g]quinazoline salt | 10.0 |
| Lactose Ph.Eur. | 488.5 |

-continued

| | |
|---|---|
| Magnesium stearate | 1.5 |
| (e) Injection I | (50 mg/ml) |
| Cyclopenta[g]quinazoline salt | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |
| (f) Injection II | (10 mg/ml) |
| Cyclopenta[g]quinazoline salt | 1.0% w/v |
| Sodium phosphate BP | 3.6% w/v |
| 0.1 M Sodium hydroxide solution | 15.0% v/v |
| Water for injection to 100% | |

-continued

| | |
|---|---|
| (g) Injection III | (1 mg/ml, buffered to pH 6) |
| Cyclopenta[g]quinazoline salt | 0.1% w/v |
| Sodium phosphate BP | 2.26% w/v |
| Citric acid | 0.38% w/v |
| Polyethylene glycol 400 | 3.5% w/v |
| Water for injection to 100% | |

The above formulations may be prepared by conventional procedures well known in the pharmaceutical art. The tablets (a) to (c) may be enteric coated by conventional means, for example with a coating of cellulose acetate phthalate.

TABLE 1

Activity of 2-substituted quinazolines and cyclopenta[g]quinazolines in human A431 and A431-FBP cell lines grown in 20 nM folate (RSLV)

| | Inhibition of cell growth, $IC_{50}$, μM 20 nM LV | | Inhibition of cell growth, $IC_{50}$, μM 20 nM LV | |
|---|---|---|---|---|
| | A431 | A431 + 1 μM FA (fold increased $IC_{50}$ in presence of folic acid) | A431-FBP (fold increased sensitivity compared with A431) | A431-FBP + 1 μM FA (fold increased $IC_{50}$ in presence of folic acid) |
| CB30195 | 0.4 ± 0.14 | 0.37 ± 0.14 (1) | 0.17 ± 0.065 | 0.23 ± 0.87 (1) |
| CB300612 | 2.2 ± 0.78 | 1.9 ± 0.65 (1) | 1.2 ± 0.17 (2) | 1.3 ± 0.23 (1) |
| CB300604 | 3.7 ± 0.71 | 3.4 ± 0.91 (1) | 0.28 ± 0.057 (13) | 1.2 ± 0.59 (4) |
| ZD9331 | 0.082 ± 0.042 | 0.067 ± 0.029 (1) | 0.018 ± 0.0097 (4) | 0.034 ± 0.0087 (2) |
| CB300512 | — | — | — | — |
| CB300533 | — | — | — | — |
| CB300395 | 0.72 ± 0.18 | 0.72 ± 0.12 (1) | 0.47 ± 0.20 (2) | 0.50 ± 0.17 (1) |
| CB300635 | 9.5 ± 5.1 | 9.7 ± 5.4 (1) | 4.1 ± 2.0 (2) | 4.3 ± 2.0 (1) |
| CB300616 | 5.9 ± 1.0 | 6.2 ± 1.6 (1) | 4.6 ± 0.40 (1) | 4.7 ± 1.1 (1) |
| CB300638 (RS) | 1.4 ± 0.23 | 1.4 ± 0.25 (1) | 0.0065 ± 0.0001 (220) | 0.87 ± 0.29 (130) |
| CB300944 (RS) | 23, 27 | 22, 25 (1) | 8.3 ± 0.64 (3) | 7.1 ± 1.0 (1) |
| CB300945 (RS) | 9.8 ± 3.4 | 9.3 ± 3.5 (1) | 0.0021 ± 0.0011 (4700) | 6.5 ± 0.86 (3100) |
| CB300960 (R,S) | 4.5 | 4.3 (1) | 0.028 | 5.1 (180) |

TABLE 2

Activity of 2-substituted quinazolines and cyclopenta[g]quinazolines in human A431 and A431-FBP cell lines grown in 1 nM folate (RSLV)

| | Inhibition of cell growth, $IC_{50}$, μM 1 nM LV | | Inhibition of cell growth, $IC_{50}$, μM 1 nM LV | |
|---|---|---|---|---|
| | A431 | A431 + 1 μM FA (fold increased $IC_{50}$ in presence of folic acid) | A431-FBP (fold increased sensitivity compared with A431) | A431-FBP + 1 μM FA (fold increased $IC_{50}$ in presence of folic acid) |
| CB30195 | 0.25 ± 0.13 | 0.21 ± 0.078 (1) | 0.10 ± 0.032 (3) | 0.22 ± 0.085 (2) |
| CB300612 | 1.8 ± 0.91 | 1.5 ± 0.51 (1) | 1.8 ± 0.68 (1) | 2.9 ± 0.55 (1) |
| CB300604 | 1.6 ± 0.36 | 2.0 ± 0.49 (1) | 0.50 ± 0.015 (3) | 1.8 ± 0.058 (4) |

TABLE 2-continued

Activity of 2-substituted quinazolines and cyclopenta[g]quinazolines in human A431 and A431-FBP cell lines grown in 1 nM folate (RSLV)

| | Inhibition of cell growth, IC$_{50}$, μM 1 nM LV | | Inhibition of cell growth, IC$_{50}$, μM 1 nM LV | |
|---|---|---|---|---|
| | A431 | A431 + 1 μM FA (fold increased IC$_{50}$ in presence of folic acid) | A431-FBP (fold increased sensitivity compared with A431) | A431-FBP + 1 μM FA (fold increased IC$_{50}$ in presence of folic acid) |
| ZD9331 | 0.061 ± 0.014 | 0.056 ± 0.025 (1) | 0.0088 ± 0.0052 (7) | 0.027 ± 0.0076 (3) |
| CB300512 | — | — | — | — |
| CB300533 | — | — | — | — |
| CB300395 | 0.70 ± 0.072 | 0.74 ± 0.053 (1) | 0.43 ± 0.36 (2) | 0.54 ± 0.34 (1) |
| CB300635 | 6.1 ± 1.3 | 6.7 ± 1.9 (1) | 2.7 ± 0.87 (2) | 3.3 ± 1.5 (1) |
| CB300616 | 4.9 ± 2.0 | 5.2 ± 2.1 (1) | 5.5 ± 3.5 (1) | 5.6 ± 3.0 (1) |
| CB300638 (RS) | 1.2 ± 0.21 | 0.98 ± 0.23 (1) | 0.0072 ± 0.001 (170) | 0.61 ± 0.012 (85) |
| CB300944 (RS) | 24 ± 3.6 | 24 ± 2.9 (1) | 9.1 ± 0.83 (3) | 12 ± 2.1 (1) |
| CB300945 (RS) | 7.2 ± 3.6 | 7.3 ± 3.3 (1) | 0.0019 ± 0.0006 (3800) | 5.7 ± 1.3 (3100) |

TABLE 3

Activity of 2-substituted quinazolines and cyclopenta[g]quinazolines in human KB cells grown in 1 and 20 nM folate (RS LV)

| | Inhibition of cell growth, IC$_{50}$, μM 1 nM LV | | Inhibition of cell growth, IC$_{50}$, μM 20 nM LV | |
|---|---|---|---|---|
| | KB | KB + 1 μM FA (fold increased IC$_{50}$ in presence of folic acid) | KB | KB + 1 μM FA (fold increased IC$_{50}$ in presence of folic acid) |
| CB30195 | 0.0053 ± 0.0006 | 0.18 ± 0.012 (34) | 0.027 ± 0.002 | 0.15 ± 0.015 (6) |
| CB300612 | 0.97 ± 0.20 | 2.2 ± 0.35 (2) | 1.7 ± 0.20 | 2.0 ± 0.25 (1) |
| CB300604 | 0.0061 ± 0.00095 | 0.69 ± 0.08 (120) | 0.035 ± 0.005 | 0.65 ± 0.04 (20) |
| ZD9331 | 0.0021 ± 0.0013 | 0.00641 ± 0.0035 (3) | 0.0036 ± 0.0021 | 0.012 ± 0.005 (3) |
| CB300512 | — | — | — | — |
| CB300533 | — | — | — | — |
| CB300395 | 0.063 ± 0.081 | 0.23 ± 0.05 (4) | 0.065 ± 0.0092 | 0.17 ± 0.032 (3) |
| CB300635 | 2.8 ± 1.1 | 3.8 ± 0.6 (1) | 3.2 ± 0.6 | 4.4 ± 0.25 (1) |
| CB300616 | 0.0037 ± 0.0018 | 0.58 ± 0.05 (160) | 0.008 ± 0.00072 | 0.59 ± 0.19 (74) |
| CB300638 (RS) | 0.0079 ± 0.001 | 0.61 ± 0.012 (76) | 0.0053 ± 0.0025 | 0.76 ± 0.17 (140) |
| CB300944 (RS) | 19 ± 0 | 19 ± 1.5 (1) | 19 ± 0.58 | 19 ± 1.2 (1) |
| CB300945 (RS) | 0.0034 ± 0.0007 | 7.6 ± 1.3 (2200) | 0.0034 ± 0.0009 | 7.3 ± 2.0 (2100) |

TABLE 4
Structures of the compounds tested—Comparative compounds
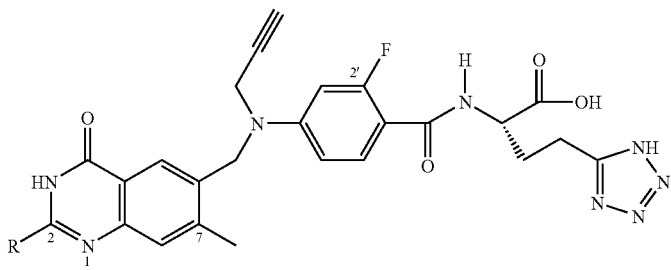
ZD9331, R = Me
CB300512, R = NH₂
CB300533, R = CH₂OH
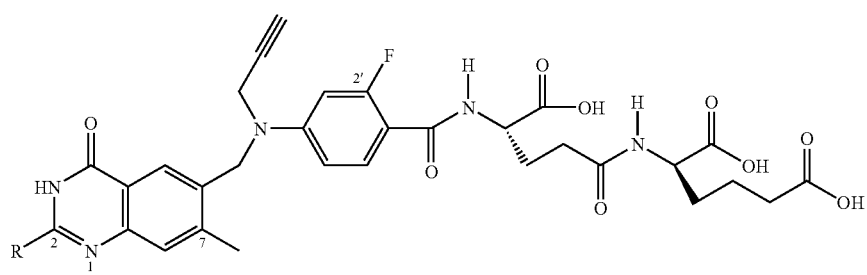
CB300395, R = Me
CB300635, R = NH₂
CB300616, R = CH₂OH
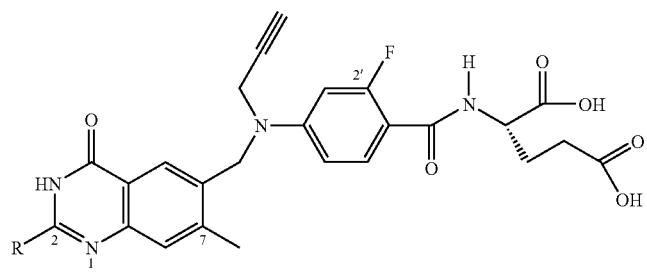
CB30195, R = Me
CB300612, R = NH₂
CB300604, R = CH₂OH
TABLE 5
Structures of the compounds tested—Compounds of the invention
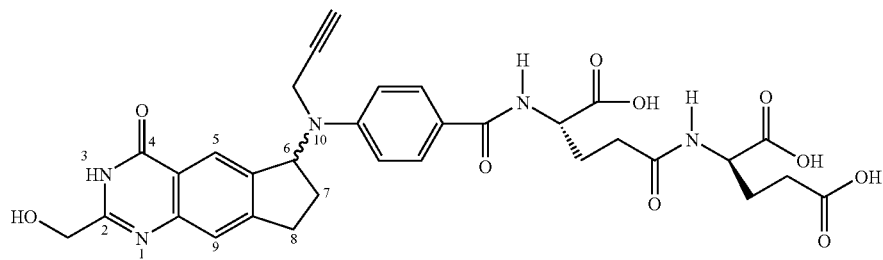
CB300945

TABLE 5-continued

Structures of the compounds tested—Compounds of the invention

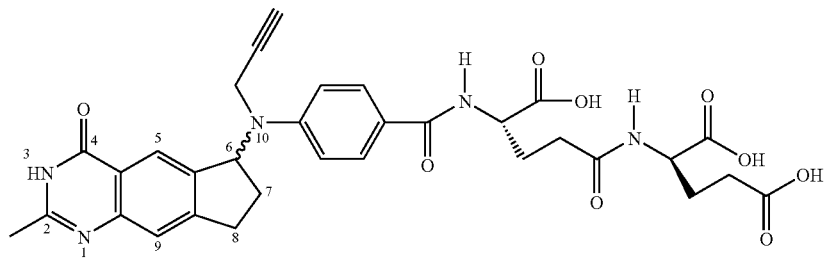

CB300638

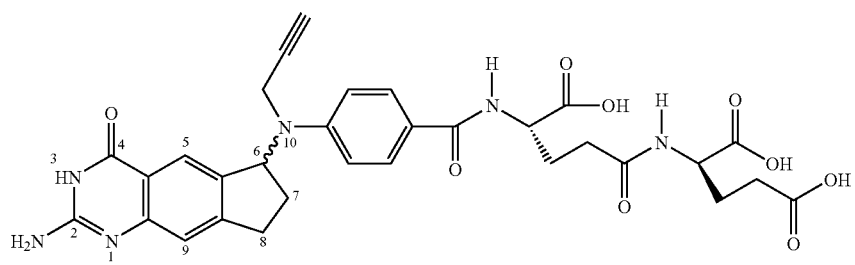

CB300944

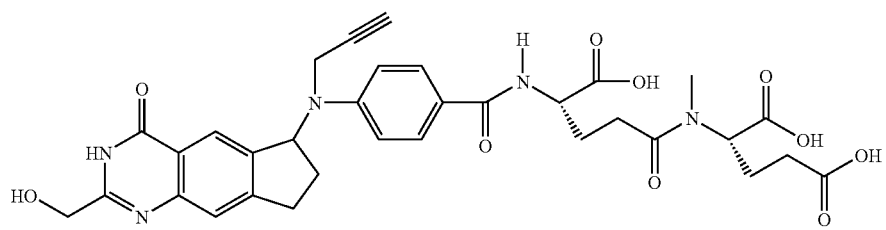

CB300960

The invention claimed is:
1. A cyclopenta[g]quinazoline wherein the compound is:
N-{N-{4-[N-(2-methoxymethyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid;
N-{N-{4-[N-(2-hydroxymethyl-4-oxo-3,4,7,8-tetrahydro-6H-cyclopenta[g]quinazolin-6-yl)-N-(prop-2-ynyl)amino]benzoyl}-L-γ-glutamyl}-D-glutamic acid; or
N-{N-{4-[N-(2-hydroxymethyl-4-oxo-3,4,7,8-tetrahydro-6H-cyclopenta[g]quinazolin-6-yl)-N-(prop-2-ynyl)amino]benzoyl}-L-γ-glutamyl}-N-methyl-L-glutamic acid;
or a pharmaceutically acceptable salt or ester thereof.
2. A pharmaceutical composition comprising a cyclopenta[g]quinazoline according to claim 1 together with a pharmaceutically acceptable diluent or carrier.

* * * * *